(12) United States Patent
Perry et al.

(10) Patent No.: US 8,396,548 B2
(45) Date of Patent: Mar. 12, 2013

(54) SELECTIVE DRUG DELIVERY IN A LUMEN

(75) Inventors: Mike Perry, Los Altos, CA (US);
Corbett W. Stone, San Diego, CA (US);
Rolfe Tyson Gustus, San Diego, CA (US); Ronda Schreiber, Poway, CA (US); Meital Mazor, San Diego, CA (US); Brian Conn, San Diego, CA (US)

(73) Assignee: Vessix Vascular, Inc., Laguna Hills, CA (US)

( * ) Notice: Subject to any disclaimer, the term of this patent is extended or adjusted under 35 U.S.C. 154(b) by 489 days.

(21) Appl. No.: 12/616,720

(22) Filed: Nov. 11, 2009

(65) Prior Publication Data
US 2010/0125239 A1 May 20, 2010

Related U.S. Application Data

(60) Provisional application No. 61/114,958, filed on Nov. 14, 2008.

(51) Int. Cl.
*A61M 25/10* (2006.01)
(52) U.S. Cl. ............... 604/21; 604/103.02; 604/509
(58) Field of Classification Search ............. 600/381; 604/20, 21, 53, 96, 99, 101, 101.04, 103.01–103.11, 604/265, 266, 509, 890.1, 892.1; 606/27, 606/32, 192, 194
See application file for complete search history.

(56) References Cited

U.S. PATENT DOCUMENTS

| 1,167,014 A | 1/1914 | O'Brien |
| 2,505,358 A | 4/1950 | Gusberg et al. |
| 2,701,559 A | 2/1955 | Cooper |
| 3,108,593 A | 10/1963 | Glassman |
| 3,108,594 A | 10/1963 | Glassman |
| 3,540,431 A | 11/1970 | Mobin-Uddin |
| 3,952,747 A | 4/1976 | Kimmell, Jr. |
| 3,996,938 A | 12/1976 | Clark, III |
| 4,046,150 A | 9/1977 | Schwartz et al. |
| 4,290,427 A | 9/1981 | Chin |
| 4,587,975 A | 5/1986 | Salo et al. |
| 4,682,596 A | 7/1987 | Bales et al. |

(Continued)

FOREIGN PATENT DOCUMENTS

| CA | 2384866 A1 | 5/2001 |
| CN | 101583323 A | 11/2009 |

(Continued)

OTHER PUBLICATIONS

Scheller et al., "Potential Solutions to the Current Problem: Coated Balloon," EuroIntervention, Aug. 2008; 4 Suppl C: C63-66.

(Continued)

*Primary Examiner* — Nicholas Lucchesi
*Assistant Examiner* — Gerald Landry, II
(74) *Attorney, Agent, or Firm* — Seager, Tufte & Wickhem, LLC

(57) ABSTRACT

Methods and systems are disclosed for selective drug or fluid delivery in a lumen through a coating or fluid delivery channels. One system includes an elongate catheter having a proximal end and a distal end with an axis therebetween, the catheter having a radially expandable balloon near the distal end and an energy delivery portion proximate the balloon for transmission of energy, a thermally changeable coating having a releasable drug coupled to the balloon, the thermally changeable coating being oriented to be urged against the body tissue when the expandable balloon expands and an energy source operatively coupled to the energy delivery portion configured to energize the energy delivery portion to heat and liquefy the thermally changeable coating to release the drug to the body tissue.

45 Claims, 4 Drawing Sheets

U.S. PATENT DOCUMENTS

| | | | |
|---|---|---|---|
| 4,709,698 A | 12/1987 | Johnston et al. | |
| 4,770,653 A | 9/1988 | Shturman | |
| 4,784,132 A | 11/1988 | Fox et al. | |
| 4,785,806 A | 11/1988 | Deckelbaum | |
| 4,799,479 A | 1/1989 | Spears | |
| 4,862,886 A | 9/1989 | Clarke et al. | |
| 4,955,377 A | 9/1990 | Lennox et al. | |
| 4,976,711 A | 12/1990 | Parins et al. | |
| 5,053,033 A | 10/1991 | Clarke | |
| 5,071,424 A | 12/1991 | Reger | |
| 5,074,871 A | 12/1991 | Groshong | |
| 5,098,429 A | 3/1992 | Sterzer | |
| 5,098,431 A | 3/1992 | Rydell | |
| 5,102,402 A | 4/1992 | Dror et al. | |
| RE33,925 E | 5/1992 | Bales et al. | |
| 5,109,859 A | 5/1992 | Jenkins | |
| 5,125,928 A | 6/1992 | Parins et al. | |
| 5,129,396 A | 7/1992 | Rosen et al. | |
| 5,156,610 A | 10/1992 | Reger | |
| 5,158,564 A | 10/1992 | Schnepp-Pesch et al. | |
| 5,178,620 A | 1/1993 | Eggers et al. | |
| 5,178,625 A | 1/1993 | Groshong | |
| 5,190,540 A | 3/1993 | Lee | |
| 5,211,651 A | 5/1993 | Reger et al. | |
| 5,263,493 A | 11/1993 | Avitall | |
| 5,277,201 A | 1/1994 | Stern | |
| 5,282,484 A | 2/1994 | Reger | |
| 5,286,254 A * | 2/1994 | Shapland et al. | 604/21 |
| 5,304,121 A * | 4/1994 | Sahatjian | 604/509 |
| 5,304,171 A | 4/1994 | Gregory et al. | |
| 5,304,173 A | 4/1994 | Kittrell et al. | |
| 5,306,250 A | 4/1994 | March et al. | |
| 5,322,064 A | 6/1994 | Lundquist | |
| 5,330,518 A | 7/1994 | Neilson et al. | |
| 5,380,319 A | 1/1995 | Saito et al. | |
| 5,383,917 A | 1/1995 | Desai et al. | |
| 5,409,000 A | 4/1995 | Imran | |
| 5,419,767 A | 5/1995 | Eggers et al. | |
| 5,453,091 A | 9/1995 | Taylor et al. | |
| 5,454,809 A | 10/1995 | Janssen | |
| 5,474,530 A | 12/1995 | Passafaro et al. | |
| 5,496,311 A | 3/1996 | Abele et al. | |
| 5,496,312 A | 3/1996 | Klicek | |
| 5,498,261 A | 3/1996 | Strul | |
| 5,540,681 A | 7/1996 | Strul et al. | |
| 5,545,161 A | 8/1996 | Imran | |
| 5,562,100 A | 10/1996 | Kittrell | |
| 5,571,122 A | 11/1996 | Kelly et al. | |
| 5,571,151 A | 11/1996 | Gregory | |
| 5,573,531 A | 11/1996 | Gregory | |
| 5,573,533 A | 11/1996 | Strul | |
| 5,588,962 A * | 12/1996 | Nicholas et al. | 604/507 |
| 5,599,346 A | 2/1997 | Edwards et al. | |
| 5,609,606 A | 3/1997 | O'Boyle | |
| 5,626,576 A | 5/1997 | Janssen | |
| 5,643,297 A | 7/1997 | Nordgren et al. | |
| 5,647,847 A | 7/1997 | Lafontaine et al. | |
| 5,649,923 A | 7/1997 | Gregory et al. | |
| 5,662,671 A | 9/1997 | Barbut et al. | |
| 5,665,062 A | 9/1997 | Houser | |
| 5,665,098 A | 9/1997 | Kelly et al. | |
| 5,681,282 A | 10/1997 | Eggers | |
| 5,693,029 A | 12/1997 | Leonhardt | |
| 5,693,043 A | 12/1997 | Kittrell et al. | |
| 5,697,369 A | 12/1997 | Long, Jr. et al. | |
| 5,697,909 A | 12/1997 | Eggers et al. | |
| 5,713,942 A | 2/1998 | Stern et al. | |
| 5,749,914 A | 5/1998 | Janssen | |
| 5,755,753 A | 5/1998 | Knowlton | |
| 5,775,338 A | 7/1998 | Hastings | |
| 5,776,174 A | 7/1998 | Van Tassel | |
| 5,792,105 A | 8/1998 | Lin et al. | |
| 5,807,306 A | 9/1998 | Shapland et al. | |
| 5,817,092 A | 10/1998 | Behl | |
| 5,817,144 A | 10/1998 | Gregory | |
| 5,848,969 A | 12/1998 | Panescu et al. | |
| 5,860,974 A | 1/1999 | Abele | |
| 5,865,801 A | 2/1999 | Houser | |
| 5,869,127 A | 2/1999 | Zhong | |
| 5,871,524 A | 2/1999 | Knowlton | |
| 5,876,369 A | 3/1999 | Houser | |
| 5,876,374 A | 3/1999 | Alba et al. | |
| 5,876,397 A | 3/1999 | Edelman et al. | |
| 5,904,651 A | 5/1999 | Swanson et al. | |
| 5,906,636 A | 5/1999 | Casscells, III et al. | |
| 5,919,219 A | 7/1999 | Knowlton | |
| 5,934,284 A | 8/1999 | Plaia et al. | |
| 5,948,011 A | 9/1999 | Knowlton | |
| 5,954,717 A | 9/1999 | Behl et al. | |
| 5,999,678 A | 12/1999 | Murphy-Chutorian et al. | |
| 6,010,522 A | 1/2000 | Barbut et al. | |
| 6,032,675 A | 3/2000 | Rubinsky | |
| 6,033,398 A | 3/2000 | Farley et al. | |
| 6,036,689 A | 3/2000 | Tu et al. | |
| 6,041,260 A | 3/2000 | Stern et al. | |
| 6,050,994 A | 4/2000 | Sherman | |
| 6,056,744 A | 5/2000 | Edwards | |
| 6,056,746 A | 5/2000 | Goble et al. | |
| 6,081,749 A | 6/2000 | Ingle et al. | |
| 6,083,159 A | 7/2000 | Driscoll et al. | |
| 6,091,995 A | 7/2000 | Ingle et al. | |
| 6,117,128 A | 9/2000 | Gregory | |
| 6,120,516 A | 9/2000 | Selmon et al. | |
| 6,123,702 A | 9/2000 | Swanson et al. | |
| 6,123,718 A | 9/2000 | Tu et al. | |
| 6,129,725 A | 10/2000 | Tu et al. | |
| 6,142,991 A | 11/2000 | Schatzberger | |
| 6,152,899 A | 11/2000 | Farley et al. | |
| 6,156,046 A | 12/2000 | Passafaro et al. | |
| 6,161,048 A | 12/2000 | Sluijter et al. | |
| 6,165,187 A | 12/2000 | Reger | |
| 6,183,468 B1 | 2/2001 | Swanson et al. | |
| 6,190,379 B1 | 2/2001 | Heuser et al. | |
| 6,191,862 B1 | 2/2001 | Swanson et al. | |
| 6,197,021 B1 | 3/2001 | Panescu et al. | |
| 6,200,266 B1 | 3/2001 | Shokrollahi et al. | |
| 6,203,561 B1 | 3/2001 | Ramee et al. | |
| 6,211,247 B1 | 4/2001 | Goodman | |
| 6,216,704 B1 | 4/2001 | Ingle et al. | |
| 6,219,577 B1 | 4/2001 | Brown, III et al. | |
| 6,228,076 B1 | 5/2001 | Winston et al. | |
| 6,231,516 B1 | 5/2001 | Keilman et al. | |
| 6,241,753 B1 | 6/2001 | Knowlton | |
| 6,258,087 B1 | 7/2001 | Edwards et al. | |
| 6,287,323 B1 | 9/2001 | Hammerslag | |
| 6,293,942 B1 | 9/2001 | Goble et al. | |
| 6,299,379 B1 | 10/2001 | Lewis | |
| 6,299,623 B1 | 10/2001 | Wulfman | |
| 6,309,379 B1 | 10/2001 | Willard et al. | |
| 6,309,399 B1 | 10/2001 | Barbut et al. | |
| 6,311,090 B1 | 10/2001 | Knowlton | |
| 6,319,242 B1 | 11/2001 | Patterson et al. | |
| 6,319,251 B1 | 11/2001 | Tu et al. | |
| 6,322,559 B1 | 11/2001 | Daulton et al. | |
| 6,325,799 B1 | 12/2001 | Goble | |
| 6,328,699 B1 | 12/2001 | Eigler et al. | |
| 6,350,276 B1 | 2/2002 | Knowlton | |
| 6,353,751 B1 | 3/2002 | Swanson et al. | |
| 6,364,840 B1 | 4/2002 | Crowley | |
| 6,377,854 B1 | 4/2002 | Knowlton | |
| 6,377,855 B1 | 4/2002 | Knowlton | |
| 6,381,497 B1 | 4/2002 | Knowlton | |
| 6,381,498 B1 | 4/2002 | Knowlton | |
| 6,387,380 B1 | 5/2002 | Knowlton | |
| 6,389,311 B1 | 5/2002 | Whayne et al. | |
| 6,389,314 B2 | 5/2002 | Feiring | |
| 6,391,024 B1 | 5/2002 | Sun et al. | |
| 6,394,956 B1 | 5/2002 | Chandrasekaran et al. | |
| 6,405,090 B1 | 6/2002 | Knowlton | |
| 6,409,723 B1 | 6/2002 | Edwards | |
| 6,413,255 B1 | 7/2002 | Stern | |
| 6,421,559 B1 | 7/2002 | Pearlman | |
| 6,423,057 B1 | 7/2002 | He et al. | |
| 6,425,912 B1 | 7/2002 | Knowlton | |
| 6,430,446 B1 | 8/2002 | Knowlton | |
| 6,438,424 B1 | 8/2002 | Knowlton | |
| 6,445,939 B1 | 9/2002 | Swanson et al. | |

| | | |
|---|---|---|
| 6,453,202 B1 | 9/2002 | Knowlton |
| 6,454,775 B1 | 9/2002 | Demarais et al. |
| 6,458,098 B1 | 10/2002 | Kanesaka |
| 6,461,378 B1 | 10/2002 | Knowlton |
| 6,470,216 B1 | 10/2002 | Knowlton |
| 6,471,689 B1 * | 10/2002 | Joseph et al. ............... 604/892.1 |
| 6,477,426 B1 | 11/2002 | Fenn et al. |
| 6,482,202 B1 | 11/2002 | Goble et al. |
| 6,485,489 B2 | 11/2002 | Teirstein et al. |
| 6,488,679 B1 | 12/2002 | Swanson et al. |
| 6,497,711 B1 | 12/2002 | Plaia et al. |
| 6,508,765 B2 | 1/2003 | Suorsa et al. |
| 6,511,496 B1 | 1/2003 | Huter et al. |
| 6,522,926 B1 | 2/2003 | Kieval et al. |
| 6,540,761 B2 | 4/2003 | Houser |
| 6,546,272 B1 | 4/2003 | MacKinnon et al. |
| 6,552,796 B2 | 4/2003 | Magnin et al. |
| 6,558,381 B2 | 5/2003 | Ingle et al. |
| 6,558,382 B2 | 5/2003 | Jahns et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,582,423 B1 | 6/2003 | Thapliyal et al. |
| 6,589,238 B2 | 7/2003 | Edwards et al. |
| 6,592,526 B1 | 7/2003 | Lenker |
| 6,605,061 B2 | 8/2003 | Vantassel et al. |
| 6,623,453 B1 | 9/2003 | Guibert et al. |
| 6,632,193 B1 | 10/2003 | Davison et al. |
| 6,632,196 B1 | 10/2003 | Houser |
| 6,673,066 B2 | 1/2004 | Werneth |
| 6,673,290 B1 | 1/2004 | Whayne et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,706,011 B1 | 3/2004 | Murphy-Chutorian et al. |
| 6,706,037 B2 | 3/2004 | Zvuloni et al. |
| 6,714,822 B2 | 3/2004 | King et al. |
| 6,720,350 B2 | 4/2004 | Kunz et al. |
| 6,723,064 B2 | 4/2004 | Babaev |
| 6,736,811 B2 | 5/2004 | Panescu et al. |
| 6,748,953 B2 | 6/2004 | Sherry et al. |
| 6,760,616 B2 | 7/2004 | Hoey et al. |
| 6,769,433 B2 | 8/2004 | Zikorus et al. |
| 6,771,996 B2 | 8/2004 | Bowe et al. |
| 6,786,904 B2 | 9/2004 | Doscher |
| 6,788,977 B2 | 9/2004 | Fenn et al. |
| 6,807,444 B2 | 10/2004 | Tu et al. |
| 6,829,497 B2 | 12/2004 | Mogul |
| 6,845,267 B2 | 1/2005 | Harrison et al. |
| 6,849,073 B2 | 2/2005 | Hoey et al. |
| 6,853,425 B2 | 2/2005 | Kim et al. |
| 6,926,716 B2 | 8/2005 | Baker et al. |
| 6,932,776 B2 | 8/2005 | Carr |
| 6,936,047 B2 | 8/2005 | Nasab et al. |
| 6,953,425 B2 | 10/2005 | Brister |
| 6,955,174 B2 | 10/2005 | Joye |
| 6,958,075 B2 | 10/2005 | Mon et al. |
| 6,962,584 B1 | 11/2005 | Stone |
| 6,964,660 B2 | 11/2005 | Maguire et al. |
| 6,972,024 B1 | 12/2005 | Kilpatrick |
| 6,991,617 B2 | 1/2006 | Hektner et al. |
| 7,008,667 B2 | 3/2006 | Chudzik et al. |
| 7,011,508 B2 | 3/2006 | Lum |
| 7,066,904 B2 * | 6/2006 | Rosenthal et al. ....... 604/103.08 |
| 7,104,987 B2 | 9/2006 | Biggs et al. |
| 7,137,980 B2 | 11/2006 | Buysse et al. |
| 7,162,303 B2 | 1/2007 | Levin et al. |
| 7,192,427 B2 | 3/2007 | Chapelon et al. |
| 7,200,445 B1 | 4/2007 | Dalbec et al. |
| 7,252,664 B2 | 8/2007 | Nasab et al. |
| 7,288,096 B2 | 10/2007 | Chin |
| 7,291,146 B2 | 11/2007 | Steinke et al. |
| 7,326,235 B2 | 2/2008 | Edwards |
| 7,407,671 B2 | 8/2008 | McBride et al. |
| 7,425,212 B1 | 9/2008 | Danek et al. |
| 7,426,409 B2 | 9/2008 | Casscells, III et al. |
| 7,497,858 B2 | 3/2009 | Chapelon et al. |
| 7,556,624 B2 | 7/2009 | Laufer et al. |
| 7,617,005 B2 | 11/2009 | Demarais et al. |
| 7,632,268 B2 | 12/2009 | Edwards et al. |
| 7,653,438 B2 | 1/2010 | Deem et al. |
| 7,691,080 B2 | 4/2010 | Seward et al. |
| 7,717,948 B2 | 5/2010 | Demarais et al. |
| 7,854,734 B2 | 12/2010 | Biggs et al. |
| 7,862,565 B2 | 1/2011 | Eder et al. |
| 7,901,400 B2 | 3/2011 | Wham et al. |
| 7,942,874 B2 | 5/2011 | Eder et al. |
| 2001/0051774 A1 | 12/2001 | Littrup et al. |
| 2002/0072686 A1 | 6/2002 | Hoey et al. |
| 2002/0077592 A1 | 6/2002 | Barry |
| 2002/0087156 A1 | 7/2002 | Maguire et al. |
| 2002/0107511 A1 | 8/2002 | Collins et al. |
| 2002/0143324 A1 | 10/2002 | Edwards |
| 2003/0004510 A1 | 1/2003 | Wham et al. |
| 2003/0028114 A1 | 2/2003 | Casscells, III et al. |
| 2003/0060857 A1 | 3/2003 | Perrson et al. |
| 2003/0060858 A1 | 3/2003 | Kieval et al. |
| 2003/0069619 A1 | 4/2003 | Fenn et al. |
| 2003/0088189 A1 | 5/2003 | Tu et al. |
| 2003/0195501 A1 | 10/2003 | Sherman et al. |
| 2003/0212394 A1 | 11/2003 | Pearson et al. |
| 2003/0220639 A1 | 11/2003 | Chapelson et al. |
| 2003/0229340 A1 | 12/2003 | Sherry et al. |
| 2003/0229384 A1 | 12/2003 | Mon |
| 2004/0006333 A1 * | 1/2004 | Arnold et al. ..................... 606/15 |
| 2004/0062852 A1 | 4/2004 | Schroeder et al. |
| 2004/0073206 A1 | 4/2004 | Foley et al. |
| 2004/0111016 A1 | 6/2004 | Casscells, III et al. |
| 2004/0181165 A1 | 9/2004 | Hoey et al. |
| 2004/0186468 A1 | 9/2004 | Edwards |
| 2004/0220556 A1 | 11/2004 | Cooper et al. |
| 2004/0243199 A1 | 12/2004 | Mon et al. |
| 2005/0010208 A1 | 1/2005 | Winston et al. |
| 2005/0015125 A1 | 1/2005 | Mioduski et al. |
| 2005/0096647 A1 | 5/2005 | Steinke et al. |
| 2005/0203434 A1 | 9/2005 | Kassab |
| 2005/0203498 A1 | 9/2005 | Mon et al. |
| 2005/0251116 A1 * | 11/2005 | Steinke et al. ..................... 606/8 |
| 2005/0283195 A1 | 12/2005 | Pastore et al. |
| 2006/0085054 A1 | 4/2006 | Zikorus et al. |
| 2006/0089638 A1 | 4/2006 | Carmel |
| 2006/0184060 A1 | 8/2006 | Belacazar et al. |
| 2006/0235286 A1 * | 10/2006 | Stone et al. ..................... 600/381 |
| 2006/0246143 A1 | 11/2006 | Ege |
| 2007/0078498 A1 | 4/2007 | Stone et al. |
| 2007/0173805 A1 | 7/2007 | Rezai et al. |
| 2007/0173899 A1 | 7/2007 | Levin et al. |
| 2007/0197891 A1 | 8/2007 | Shachar et al. |
| 2007/0265687 A1 | 11/2007 | Deem et al. |
| 2007/0278103 A1 | 12/2007 | Hoerr et al. |
| 2008/0125772 A1 | 5/2008 | Stone et al. |
| 2008/0140002 A1 | 6/2008 | Ramzipoor et al. |
| 2008/0161801 A1 | 7/2008 | Steinke et al. |
| 2008/0188912 A1 | 8/2008 | Stone et al. |
| 2008/0188913 A1 | 8/2008 | Stone et al. |
| 2008/0262489 A1 | 10/2008 | Steinke et al. |
| 2008/0269664 A1 * | 10/2008 | Trovato et al. ..................... 604/20 |
| 2009/0018609 A1 | 1/2009 | DeLorenzo |
| 2009/0062873 A1 | 3/2009 | Wu et al. |
| 2009/0074828 A1 | 3/2009 | Alexis et al. |
| 2010/0076299 A1 | 3/2010 | Gustus et al. |
| 2010/0125268 A1 | 5/2010 | Gustus et al. |
| 2010/0137952 A1 | 6/2010 | Demarais et al. |
| 2010/0160906 A1 | 6/2010 | Jarrard |
| 2010/0204560 A1 | 8/2010 | Salahieh et al. |
| 2010/0286684 A1 | 11/2010 | Hata et al. |
| 2010/0324472 A1 * | 12/2010 | Wulfman ........................ 604/22 |
| 2011/0092880 A1 | 4/2011 | Gertner |
| 2011/0104061 A1 | 5/2011 | Seward |
| 2011/0118598 A1 | 5/2011 | Gertner |
| 2011/0118600 A1 | 5/2011 | Gertner |
| 2011/0118726 A1 | 5/2011 | De La Rama |
| 2011/0178403 A1 | 7/2011 | Weng et al. |
| 2011/0207758 A1 | 8/2011 | Sobotka |
| 2011/0270238 A1 | 11/2011 | Rizq et al. |
| 2011/0306851 A1 | 12/2011 | Wang |
| 2011/0307034 A1 | 12/2011 | Hastings et al. |
| 2011/0319809 A1 | 12/2011 | Smith |

| | | | |
|---|---|---|---|
| 2012/0029496 A1 | 2/2012 | Smith | |
| 2012/0029500 A1 | 2/2012 | Jenson | |
| 2012/0029509 A1 | 2/2012 | Smith | |
| 2012/0029511 A1 | 2/2012 | Smith | |
| 2012/0029512 A1 | 2/2012 | Willard et al. | |

FOREIGN PATENT DOCUMENTS

| | | |
|---|---|---|
| CN | 102271607 A | 12/2011 |
| DE | 102005041601 A1 | 4/2007 |
| DE | 102008048616 A1 | 4/2010 |
| EP | 558297 A2 | 9/1993 |
| EP | 647435 A1 | 4/1995 |
| EP | 634910 B1 | 6/1997 |
| EP | 868884 A2 | 10/1998 |
| EP | 1005838 A1 | 6/2000 |
| EP | 1053720 A1 | 11/2000 |
| EP | 1064886 A1 | 1/2001 |
| EP | 1181895 A2 | 2/2002 |
| EP | 1297795 A1 | 6/2002 |
| EP | 1264613 A2 | 12/2002 |
| EP | 1286625 A1 | 3/2003 |
| EP | 1332724 A1 | 8/2003 |
| EP | 866675 B1 | 10/2003 |
| EP | 1433448 A1 | 6/2004 |
| EP | 1442719 A1 | 8/2004 |
| EP | 1547537 A1 | 6/2005 |
| EP | 1622531 | 2/2006 |
| EP | 1634542 A1 | 3/2006 |
| EP | 1698296 A1 | 6/2006 |
| EP | 1709922 A1 | 10/2006 |
| EP | 1946712 A1 | 7/2008 |
| EP | 1961394 A2 | 8/2008 |
| EP | 1715798 B1 | 4/2009 |
| EP | 2092957 A1 | 8/2009 |
| EP | 2208506 A1 | 7/2010 |
| EP | 2241279 A1 | 10/2010 |
| EP | 2329859 A1 | 6/2011 |
| GB | 2313062 A | 11/1997 |
| GB | 2453601 A | 4/2009 |
| JP | 2003-510126 A | 3/2003 |
| WO | WO 91/03207 A1 | 3/1991 |
| WO | WO 91/17731 A1 | 11/1991 |
| WO | WO 93/20747 A1 | 10/1993 |
| WO | WO 93/20770 A2 | 10/1993 |
| WO | WO 94/18896 A1 | 9/1994 |
| WO | WO 94/28809 A1 | 12/1994 |
| WO | WO 95/01751 A1 | 1/1995 |
| WO | WO 95/31142 A1 | 11/1995 |
| WO | WO 96/34559 A1 | 11/1996 |
| WO | WO 97/03604 A1 | 2/1997 |
| WO | WO 97/17104 A1 | 5/1997 |
| WO | WO 97/20510 A1 | 6/1997 |
| WO | WO 97/32532 A1 | 9/1997 |
| WO | WO 97/40760 A1 | 11/1997 |
| WO | WO 97/45156 A2 | 12/1997 |
| WO | WO 98/18393 A1 | 5/1998 |
| WO | WO 98/34565 A1 | 8/1998 |
| WO | WO 98/35638 A1 | 8/1998 |
| WO | WO 98/40023 A1 | 9/1998 |
| WO | WO 99/00060 A1 | 1/1999 |
| WO | WO 99/16370 A1 | 4/1999 |
| WO | WO 99/21608 A1 | 5/1999 |
| WO | WO 99/34741 A1 | 7/1999 |
| WO | WO 99/44522 A1 | 9/1999 |
| WO | WO 00/10475 A1 | 3/2000 |
| WO | WO 00/51513 A1 | 9/2000 |
| WO | WO 00/59394 A1 | 10/2000 |
| WO | WO 00/62727 A1 | 10/2000 |
| WO | WO 00/64387 A1 | 11/2000 |
| WO | WO 00/69376 A1 | 11/2000 |
| WO | WO 00/72909 A1 | 12/2000 |
| WO | WO 01/22897 A1 | 4/2001 |
| WO | WO 01/37746 A1 | 5/2001 |
| WO | WO 01/87172 A1 | 5/2001 |
| WO | WO 01/87154 A1 | 11/2001 |
| WO | WO 01/95820 A1 | 12/2001 |
| WO | WO 02/28475 A1 | 4/2002 |
| WO | WO 02/39915 A1 | 5/2002 |
| WO | WO 02/058549 A1 | 8/2002 |
| WO | WO 02/080766 A2 | 10/2002 |
| WO | WO 02/087679 A2 | 11/2002 |
| WO | WO 02/089686 A1 | 11/2002 |
| WO | WO 03/077781 A1 | 9/2003 |
| WO | WO 2004/047659 A2 | 6/2004 |
| WO | WO 2004/049976 A1 | 6/2004 |
| WO | WO 2004/064606 A2 | 8/2004 |
| WO | WO 2004/069300 A2 | 8/2004 |
| WO | WO 2004/076146 A2 | 9/2004 |
| WO | WO 2004/098694 A1 | 11/2004 |
| WO | WO 2004/105807 A2 | 12/2004 |
| WO | 2005/007000 | 1/2005 |
| WO | WO 2005/037070 A2 | 4/2005 |
| WO | WO 2005/041748 A2 | 5/2005 |
| WO | WO 2005/074829 A1 | 8/2005 |
| WO | WO 2006/041881 A2 | 4/2006 |
| WO | WO 2006/105121 A2 | 10/2006 |
| WO | WO 2006/116198 A2 | 11/2006 |
| WO | WO 2007/011634 A1 | 1/2007 |
| WO | WO 2007/014063 A2 | 2/2007 |
| WO | WO 2007/047870 A2 | 4/2007 |
| WO | WO 2007/113865 A1 | 10/2007 |
| WO | WO 2007/135431 A2 | 11/2007 |
| WO | WO 2007/146215 A2 | 12/2007 |
| WO | WO 2008/003058 A1 | 1/2008 |
| WO | WO 2008/009972 A2 | 1/2008 |
| WO | WO 2008/010150 A2 | 1/2008 |
| WO | WO 2008/036281 A2 | 3/2008 |
| WO | WO 2008/049084 A2 | 4/2008 |
| WO | WO 2008/061152 A2 | 5/2008 |
| WO | WO 2008/102363 A2 | 8/2008 |
| WO | WO 2009/036471 A1 | 3/2009 |
| WO | WO 2009/082635 A1 | 7/2009 |
| WO | WO 2009/088678 A1 | 7/2009 |
| WO | WO 2009/113064 A2 | 9/2009 |
| WO | 2009/121017 | 10/2009 |
| WO | WO 2009/137819 A1 | 11/2009 |
| WO | WO 2010/042653 A1 | 4/2010 |
| WO | WO 2010/048007 A1 | 4/2010 |
| WO | WO 2010/056771 A1 | 5/2010 |
| WO | WO 2010/057043 A1 | 5/2010 |
| WO | WO 2010/070766 A1 | 6/2010 |
| WO | WO 2010/099207 A1 | 9/2010 |
| WO | WO 2010/120944 A2 | 10/2010 |
| WO | WO 2010/134503 A1 | 11/2010 |
| WO | WO 2011/055143 A2 | 5/2011 |
| WO | WO 2011/060339 A1 | 5/2011 |
| WO | WO 2011/126580 A2 | 10/2011 |

OTHER PUBLICATIONS

Tepe et al., "Local Delivery of Paclitaxel to Inhibit Restenosis During Angioplasty of the Leg," N Engl J Med, Feb. 14, 2008; 358(7): 689-699; retrieved from the Internet: <<http://content.nejm.org/cgi/reprint/358/7/689.pdf>>.

International Search Report and Written Opinion of PCT Application No. PCT/US09/64465, mailed Jan. 13, 2010, 13 pages total.

Brown et al., "Radiofrequency capacitive heaters: the effect of coupling medium resistivity on power absorption along a mouse leg" Phys Med Biol 1993, 38 1-12 (abstract).

Cardiovascular Technologies, Inc., "Heated Balloon Device Technology" [Presentation], 2007-2008, 11 pages total. Retrieved from: <<http://www.cvtechinc.com/pr/presoCVT_Heated_Balloon_Tech.pdf>>.

Carrington, "Future of CVI: It's All About the Plaque." Diagnostic Imaging Special Edition Forum [online] [retrieved on Sep. 3, 2003] Retreived from the Internet:,http://dimag.com/specialedition/cardiacimg.shtml> 5 pages total.

Cimino, "Preventing Plaque Attack", [online] [retrieved on Sep. 3, 2003] Retrieved from the Internet: <http://Masshightech.com/displayarticledetail.ap?art_id=52283&cat_id=10>, 3 pages total.

Dahm et al, "Relation of Degree of Laser Debulking of In-Stent Restenosis as a Predictor of Restenosis Rate", Am J Cardiol, 2002; 90(1): 68-70.

De Korte C L. et al., "Characterization of Placque Components with Intravascular Ultrasound Elastography in Human Femoral and Coronary Arteries in Vitro," Circulation 2000;102:617-623.

Durney C., et al., Radiofrequency Radiation Dosimetry Handbook (with table of contents), Oct. 1986, 4th ed., 7 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/handbook/home.htm.

Fournier-Desseux et al. "Assessment of 1-lead and 2-lead electrode patterns in electrical impedance endotomography", Physiol. Meas. (2005) 26:337-349.

Fujimori et al., "Significant Prevention of In-Stent Restenosis by Evans Blue in Patients with Acute Myocardial Infarction", Abstract #2925, *AHA* (2002), 1 page total.

Fujita, "Sarpogrelate, An Antagonist of $5-HT_{2a}$ Receptor Treatment Reduces Restenosis After Coronary Stenting", Abstract #2927, *AHA* (2002), 1 page total.

Gabriel C, et al., Compilation of the Dielectric Properties of Body Tissues at RF and Microwave Frequencies (with table of contents), Jun. 1996, 17 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Report/Report.html.

Gabriel C, et al., Compilation of the Dielectric Properties of Body Tissues at RF and Microwave Frequencies, Appendi04-10-2009 A, Jun. 1996, 21 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Appendi04-10-2009.A/Appendi04-10-2009 A.html.

Gabriel C, et al., Compilation of the Dielectric Properties of Body Tissues at RF and Microwave Frequencies, Appendi04-10-2009 C, Jun. 1996, 6 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Appendi04-10-2009.C/Appendi04-10-2009. C.html.

Gregory et al., "Liquid Core Light Guide for Laser Angioplasty", *Journal of Quantum Electronics*, vol. 26, No. 12, (Dec. 1990), pp. 2289-2296.

Intraluminal, Product description [online] [retrieved on Sep. 3, 2003] Retrieved from the Internet: http://www.intraluminal.com/products/inde04-10-2009 .html> 1 page total.

Kaplan et al., "Healing after arterial dilatation with radiofrequency thermal and nonthermal balloon angioplasty systems," J Invest Surg. 1993 Jan-Feb;6(1):33-52.

Kolata, "New Studies Question Value of Opening Arteries", New York Times [online] [retrieved on Jan. 25, 2005]. Retrieved from the Internet: <http://nytimes.com/2004/03/21/health/21HEAR. html?ei=5070&en=641bc03214e&e04-10-2009=11067>, 5 pages total.

Konings M K, et al., "Development of an Intravascular Impedance Catheter for Detection of Fatty Lesions in Arteries," IEEE Transactions on Medical Imaging, vol. 51, No. 4, Apr. 2004.

Kurtz et al., "Lamellar Refractive Surgery with Scanned Intrastromal Picosecond and Femtosecond Laser Pulses in Animal Eyes", *J Refract Surg*, vol. 14, (Sep./Oct. 1998), pp. 541-548.

Lightlab Imaging Technology, "Advantages of OCT", [online] [retrieved on Sep. 3, 2003]. Retrieved from the Internet: <http:www.lightlabimaging.com/advantage.html> 2 pages total.

Lightlab Imaging Technology, "Image Gallery", [online] [retrieved on Sep. 3, 2003]. Retrieved from the Internet: <http:lightlabimaging.com/gallery/cvpstill.html> 4 pages total.

Lightlab Imaging Technology, "LightLab Imaging Starts US Cardiology Clinical Investigations", LightLab Company Press Release, [online] [retrieved on Sep. 3, 2003]. Retrieved from the Internet: <http://www.lighlabimaging.com/press/cardtrails.html> 2 pages total.

Lightlab Imaging Technology, "LightLab Sees Bright Prospects for Cardiac Application of OCT Technology" *The Graysheet Medical Devices Diagnostics & Instrumentation*, vol. 27, No. 35, (Aug. 27, 2001) [online] [retrieved on Sep. 3, 2003]. Retrieved from the Internet: <http://www.lighlabimaging.com/press/graysheet.html> 1 page total.

Lightlab Imaging Technology, "What is OCT?", [online] [retrieved on Sep. 3, 2003]. Retrieved from the Internet: <http:lightlabimaging.com/oct.html.> 2 pages total.

Lightlab Imaging Technology, "Why use Oct?", [online] [retrieved on Sep. 3, 2003]. Retrieved from the Internet: <http:lightlabimaging.com/whyoct.html> 2 pages total.

Lima et al., "Efficacy and Safety of Oral Sirolimus to Treat and Prevent In-Stent Restenosis: A Pilot Study Results", Abstract #2929, *AHA* (2002), 1 page total.

Lima et al., "Systemic Immunosuppression Inhibits In-Stent Coronary Intimal Proliferation in Renal Transplant Patients", Abstract #2928, *AHA* (2002), 1 page total.

MIT Techtalk, "Laser Catheter to Aid Coronary Surgery", Jan. 9, 1991 [online] [retrieved on Feb. 7, 2005]. Retrieved from the Internet : <http://web.mit.edu/newsoffice/tt/1991/jan09/24037. html> 4 pages total.

Morice et al., "A Randomized Comparison of a Sirolimus-Eluting Stent With a Standard Stent for Coronary Revascularization", *N. Engl J Med*, vol. 346, No. 23, (Jun. 6, 2002), pp. 1773-1779.

Müller et al., "Effectiveness and Safety of Ultrasonic Atherosclerotic Plaque Ablation: in Vitro Investigation", *CardioVas. Intervent. Radiol.*, (1993) 16: 303-307.

Nair A, et al., "Regularized Autoregressive Analysis of Intravascular Ultrasound Backscatter: Improvement in Spatial Accuracy of Tissue Maps," IEEE Transactions on Ultrasonics, Ferroelectrics, and Frequency Control, vol. 51 No. 4, Apr. 2004.

Popma et al., "Chapter 38—Percutaneous Coronary and Valvular Intervention", Heart Disease: A Textbook of Cardiovascular Medicine, 6th ed., (2001) W.B> Saunders Company, pp. 1364-1405.

Romer et al., "Histopathology of Human Coronary Atherosclerosis by Quantifying Its Chemical Composition with Raman Spectroscopy," Circulation 97:878-885 (1998).

Scheller, "Intracoronary Paclitaxel Added to Contrast Media Inhibits In-Stent Restenosis of Porcine Coronary Arteries", Abstract #2227, *AHA* (2002), 2 pages total.

Shaffer, "Scientific Basis of Laser Energy", *Clin Sports Med* 2002; 21(4):585-598.

Shmatukha a V, et al., "MRI temperature mapping during thermal balloon angioplasty," Phys Med Biol 51, (2006) N163-N171.

Slager et al., "Vaporization of Atherosclerotic Placques by Spark Erosion," J Am Coll Cardiol, vol. 5 (Jun. 1985) pp. 1382-1386.

Stiles et al., "Simulated Charactization of Atherosclerotic Lesions in the Coronary Arteries by Measurement of Bioimpedance," IEEE Transactions on Biomedical Engineering, (Jul. 2003), 5(4):916-921.

Süselbeck et al. "Intravascular electric impedance spectroscopy of atherosclerotic lesions using a new impedance system", Basic Res Cardiol (2005) 100:446-452.

Suselbeck T, et al., "In vivo intravascular electrical impedance spectroscopy using a new catheter with integrated microelectrodes," Basic Res Cardiol 100:28-34 (2005).

Van Den Berg, "Light Echoes Image the Human Body", *OLE*, Oct. 2001, pp. 35-37.

Volcano Therapeutics, "Product—Functional Measurement", [online] [retrieved on Sep. 3, 2003]. Retrieved from the Internet: <http://www.volcanotherapeutics.com/pages/products/functional_measurement-us.html> 2 pages total.

Examiners Report of Canadian Patent Application No. 2,539,026, mailed Feb. 6, 2012, 4 pages total.

Office Action issued in Chinese Patent Application No. 200480030163.9, mailed Jan. 16, 2009, 8 pages total.

Office Action issued in Chinese Patent Application No. 200480030163.9, mailed Mar. 28, 2008, 7 pages total.

Office Action issued in Chinese Patent Application No. 200480030163.9, mailed Aug. 31, 2007, 8 pages total.

Office Action issued in Chinese Patent Application No. 200480030163.9, mailed Jul. 31, 2009, 5 pages total.

Supplementary Partial European Search Report of Application No. 04816863.7, mailed May 8, 2009, 7 pages total.

Office Action issued in European Application No. 04816863.7, mailed Jun. 4, 2010, 5 pages total.

Office Action issued in European Application No. 04816863.7, mailed Dec. 5, 2011, 4 pages total.
Office Action issued in European Application No. 04816863.7, mailed Jan. 22, 2010, 6 pages total.
Formal Inquiry issued in Japanese Patent Application No. 2006-526351, mailed Jan. 17, 2012, 5 pages total.
Notice of the Reason for Refusal issued in Japanese Patent Application No. 2006-526351, mailed Apr. 27, 2010, 6 pages total.
Final Decision of Rejection issued in Japanese Patent Application No. 2006-526351, mailed Jan. 18, 2011, 4 pages total.
European Search Report and Search Opinion of EP Patent Application No. 12151957.3, mailed Apr. 16, 2012, 8 pages total.
Office Action issued in Chinese Patent Application No. 200680016424.0, mailed Apr. 13, 2010, 10 pages total.
European Search Report and Search Opinion of EP Patent Application No. 06748830.4, mailed Nov. 16, 2009, 12 pages total.
Partial European Search Report of EP Patent Application No. 11191822.3, mailed Mar. 19, 2012, 7 pages total.
Office Action issued in Chinese Patent Application No. 20111031923.X, mailed Nov. 17, 2011, 16 pages total.
Office Action issued in Chinese Patent Application No. 20111031923.X, mailed May 22, 2012, 10 pages total.
Examiners First Report of Australian Patent Application No. 2007310988, mailed May 23, 2012, 4 pages total.

European Search Report and Search Opinion of EP Patent Application No. 07844421.3, mailed Jan. 4, 2010, 15 pages total.
European Search Report and Search Opinion of EP Patent Application No. 12155447.1, mailed May 10, 2012, 6 pages total.
International Search Report and Written Opinion of PCT Application No. PCT/US2009/064027, mailed Jan. 19, 2010, 9 pages total.
European Search Report and Search Opinion of EP Patent Application No. 07844417.1, mailed Nov. 5, 2009.
European Search Report and Search Opinion of EP Patent Application No. 12154120.5, mailed May 8, 2012, 8 pages total.
European Search Report and Search Opinion of EP Patent Application No. 07844424.7, mailed Nov. 11, 2009, 11 pages total.
Partial European Search Report of EP Patent Application No. 12154069.4, mailed May 10, 2012, 5 pages total.
International Search Report of PCT Application No. PCT/US09/57728, mailed Nov. 30, 2009, 10 pages total. (2410PC).
International Search Report and Written Opinion of PCT/US2010/034789, mailed Jul. 9, 2010, 13 pages total.
International Search Report and Written Opinion of PCT/US2011/00661, mailed Nov. 18, 2011, 14 pages total.

* cited by examiner

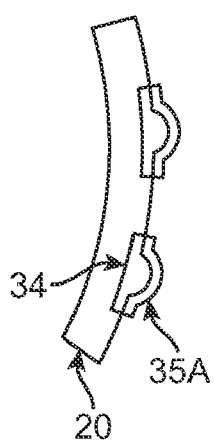
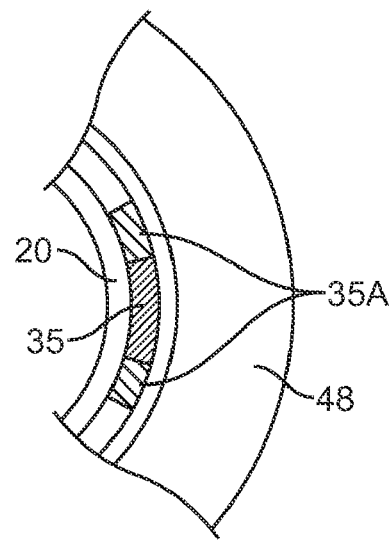
FIG. 4A
FIG. 4B
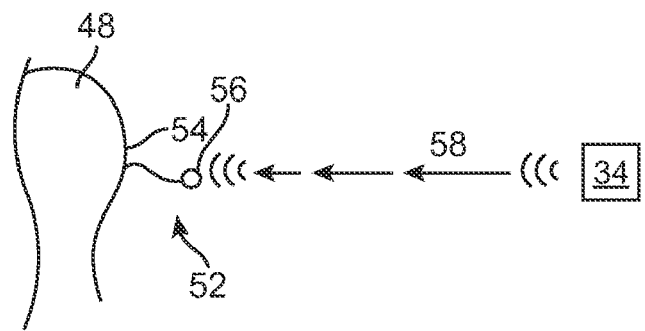
FIG. 5
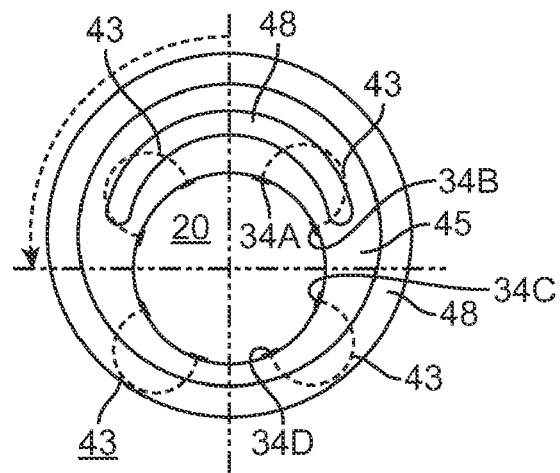
FIG. 6

SELECTIVE DRUG DELIVERY IN A LUMEN

CROSS-REFERENCES TO RELATED APPLICATIONS

The present application claims the benefit under 35 USC 119(e) of U.S. Provisional Application No. 61/114,958 filed Nov. 14, 2008; the full disclosure of which is incorporated herein by reference in their entirety.

STATEMENT AS TO RIGHTS TO INVENTIONS MADE UNDER FEDERALLY SPONSORED RESEARCH AND DEVELOPMENT

Not Applicable

BACKGROUND OF THE INVENTION

The present invention is generally related to medical devices, systems, and methods. In particular, the invention provides methods and systems for selective drug delivery to body tissue disposed about a lumen using a catheter-based treatment system.

Physicians use catheters to gain access to and repair interior tissues of the body, particularly within the lumens of the body such as blood vessels. For example, balloon angioplasty and other catheters often are used to open arteries that have been narrowed due to atherosclerotic disease. Balloon angioplasty is often effective at opening an occluded blood vessel, but the trauma associated with balloon dilation can impose significant injury, so that the benefits of balloon dilation may be limited in time.

Stenting, in conjunction with balloon dilation, is often the preferred treatment for atherosclerosis. In stenting, a collapsed metal framework is mounted on a balloon catheter which is introduced into the body. The stent is manipulated into the site of occlusion and expanded in place by the dilation of the underlying balloon. Stenting has gained widespread acceptance, and produces generally acceptable results in many cases. Along with treatment of blood vessels (particularly the coronary arteries), stents can also be used in treating many other tubular obstructions within the body, such as for treatment of reproductive, gastrointestinal, and pulmonary obstructions. Restenosis or a subsequent narrowing of the body lumen after stenting has occurred in a significant number of cases.

A variety of modified restenosis treatments or restenosis-inhibiting treatment modalities have also been proposed, including intravascular radiation, cryogenic treatments, ultrasound energy, and the like, often in combination with balloon angioplasty and/or stenting. While these and different approaches show varying degrees of promise for decreasing the subsequent degradation in blood flow following angioplasty and stenting, the trauma initially imposed on the tissues by angioplasty remains problematic.

A number of alternatives to stenting and balloon angioplasty have been proposed to open stenosed arteries. For example, a wide variety of atherectomy devices and techniques have been disclosed and attempted. Despite the disadvantages and limitations of angioplasty and stenting, atherectomy has not gained the widespread use and success rates of dilation-based approaches. More recently, still further disadvantages of dilation have come to light. These include the existence of vulnerable plaque, which can rupture and release materials that may cause myocardial infarction or heart attack.

More recently, drug coated stents (such as Johnson and Johnson's Cypher stent, the associated drug comprising Sirolimus) have demonstrated a markedly reduced restenosis rate, and others are developing and commercializing alternative drug eluting stents. While drug eluting stents appear to offer significant promise for treatment of atherosclerosis in many patients, there remain many cases where stents either cannot be used or present significant disadvantages. Generally, stenting leaves an implant in the body. Such implants can present risks, including mechanical fatigue, corrosion, thrombus formation, and the like, particularly when removal of the implant is difficult and involves invasive surgery. Stenting may have additional disadvantages for treating diffuse artery disease, for treating bifurcations, for treating areas of the body susceptible to crush, and for treating arteries subject to torsion, elongation, and shortening.

In light of the above, it would be advantageous to provide methods and systems for selective fluid delivery to artery tissue that avoids the drawbacks associated with drug eluding stents and the devices described above.

BRIEF SUMMARY OF THE INVENTION

The present invention generally provides devices, systems, and methods for selective drug or fluid delivery to a body tissue being disposed about a lumen.

In a first aspect, the invention comprises a system for selective drug delivery to a body tissue being disposed about a lumen. The system includes an elongated flexible catheter body having a proximal end and a distal end with a radially expandable balloon near the distal end of the catheter body. An energy delivery surface disposed about the expandable balloon and a thermally changeable drug coating is coupled to the balloon, the energy delivery surface and the thermally changeable coating being oriented to be urged against the body tissue when the expandable balloon expands. An energy source is operatively coupled to the energy delivery surface configured to energize the energy delivery surface to heat and liquefy the thermally changeable coating to release the drug to the body tissue.

In another aspect, the invention comprises a method for selective drug delivery in a lumen. The method includes engaging a body tissue disposed about the lumen with an energy delivery surface and a thermally changeable coating having a releasable drug disposed on a radially expandable balloon near a distal end of a catheter when the expandable balloon expands, selectively energizing the energy delivery surface to heat and liquefy portions of the thermally changeable drug coating, and releasing a drug from the coating into the body tissue.

In many embodiments, the energy delivery surface comprises a plurality of electrodes, the energy source operatively coupled to the plurality of electrodes so as to selectively energize electrode pairs to heat and liquefy portions of the thermally changeable coating between the electrode pairs to release the drug to the body tissue. In many embodiments the body tissue of the lumen includes a diseased portion and select electrode pairs are energized to selectively heat the thermally changeable coating proximate the diseased portion.

In many embodiments, the energy delivery surface comprises a plurality of electrodes disposed about the expandable balloon so as to define a plurality of remodeling zones in the tissue when the balloon is expanded within the lumen, the electrodes are radially coupled with the tissue, and energy is transmitted between the electrodes and the tissue.

In many embodiments, further comprising a tissue analyzer configured to characterize the body tissue.

In many embodiments, the energy delivery surface is energized to heat the thermally changeable coating to release the drug in responses to the characterized body tissue.

In many embodiments, the body tissue of the lumen includes a diseased portion and select electrode pairs are energized to selectively heat the thermally changeable coating proximate the diseased portion.

In many embodiments, the energy delivery surface is energized to heat the body tissue in combination with the drug delivery.

In many embodiments, the thermally changeable drug coating includes more than one drug In many embodiments, the drug is selected from at least one of, a therapeutic fluid, an anesthetic drug, a therapeutic drug, a small molecule, a gene therapeutic compound, an anti-thrombolytic agent, a lubricant (to allow higher temperatures without sticking), an electrically conductive compound to lower the impedance at the electrode, an electrically insulating compound to prevent treatment to tissue that does not need treatment, an electrically conductive compound that is intended to migrate through the endothelial layers of tissue to carry energy to the interstitial layers, or a combination of the above.

In another aspect, the invention comprises a catheter system for drug delivery to a body tissue being disposed about a lumen. The system includes an elongated flexible catheter body having a proximal end and a distal end, a radially expandable balloon near the distal end of the catheter body, and an energy delivery surface disposed about the expandable balloon. A plurality of biomolecules having a thermally releasable drug portion and an inert portion covalently bound to the balloon and an energy source operatively coupled to the energy delivery surface so as to heat the biomolecules to release the drug portion to the body tissue.

In another aspect, the invention comprises a method for fluid delivery in a lumen. The method includes engaging a body tissue disposed about the lumen with an energy delivery surface and a plurality of biomolecules having a thermally releasable drug portion and an inert portion covalently bound to the balloon near a distal end of a catheter when the expandable balloon expands, energizing the energy delivery surface to heat the biomolecules, and releasing the drug portion from the biomolecules into the body tissue.

In many embodiments, the energy delivery surface comprises a plurality of electrodes, the energy source operatively coupled to the plurality of electrodes so as to selectively energize electrode pairs to heat the biomolecules between the electrode pairs to release the drug portion to the body tissue.

In many embodiments, the body tissue of the lumen includes a diseased portion and select electrode pairs are energized to selectively heat the biomolecules proximate the to the diseased portion.

In many embodiments, the energy delivery surface and biomolecules are oriented to be urged against the body tissue when the expandable balloon expands.

In many embodiments, further comprising a tissue analyzer configured to characterize the body tissue and the energy delivery surface is energized to heat the biomolecules to release the drug portion in responses to the characterized body tissue.

In many embodiments, the energy delivery surface is further energized to heat the body tissue in combination with the drug delivery.

In many embodiments, the biomolecules include more than one releasable drug.

In many embodiments, the drug portion is selected from at least one of, a therapeutic fluid, an anesthetic drug, a therapeutic drug, a small molecule, a gene therapeutic compound, an anti-thrombolytic agent, a lubricant (to allow higher temperatures without sticking), an electrically conductive compound to lower the impedance at the electrode, an electrically insulating compound to prevent treatment to tissue that does not need treatment, an electrically conductive compound that is intended to migrate through the endothelial layers of tissue to carry energy to the interstitial layers, or a combination of the above.

In another aspect, the invention comprises a catheter system for selective fluid delivery to a body tissue being disposed about a lumen. The system includes an elongated flexible catheter body having a proximal end and a distal end, a radially expandable structure near the distal end of the catheter body, a plurality of fluid delivery channels oriented to be urged against the body tissue when the expandable structure expands, the fluid delivery channels being initially blocked with a thermally changeable material, and an energy source connector operatively coupled to the fluid delivery channels so as to heat and liquefy the thermally changeable material to selectively open one or more of the fluid delivery channels for fluid release.

In another aspect, the invention comprises a catheter system for selective fluid delivery to a body tissue being disposed about a lumen. The system includes an elongated flexible catheter body having a proximal end and a distal end, a radially expandable structure near the distal end of the catheter body, a plurality of fluid delivery channels oriented to be urged against the body tissue of the lumen when the expandable structure expands, the fluid delivery channels being initially closed, and a plurality of micro-electromechanical systems (MEMS) coupled to the fluid delivery channels to selectively open one or more fluid delivery channels and release a fluid in the lumen.

In another aspect, the invention comprises a method for selective fluid delivery in a lumen. The method includes engaging a body tissue disposed about the lumen with a plurality of fluid delivery channels on a radially expandable structure near a distal end of a catheter when the expandable structure expands, selectively opening one or more fluid delivery channels, and releasing a fluid from the select fluid delivery channels into the lumen.

In many embodiments, the plurality of fluid delivery channels protrude from the expandable structure to penetrate the body tissue of the lumen.

In many embodiments, further comprising a tissue analyzer configured to characterize the body tissue to identify body tissue to be treated and selectively opening or closing one or more fluid delivery channels in responses to the characterized body tissue to treat the identified body tissue.

In many embodiments, the fluid delivery channels can be selectively energized to selectively open one or more fluid delivery channels in responses to the characterized body tissue.

In many embodiments, the radially expandable structure comprises a balloon and the fluid delivery channels are mounted on a circumference of the balloon.

In many embodiments, the radially expandable structure comprises an expandable basket and the fluid delivery channels are mounted on a circumference of the basket.

In many embodiments, the body tissue of the lumen includes a diseased portion and select electrodes are energized to selectively open one or more fluid delivery channels proximate the diseased portion.

In many embodiments, select electrodes are energized to heat the body tissue in conjunction with the release of the fluid in the lumen.

In many embodiments, selectively opening one or more fluid delivery channels comprises selectively energizing electrodes coupled to the select fluid delivery channels to heat the select fluid delivery channels to liquefy a thermal material initially closing the fluid delivery channel.

In many embodiments, the fluid is selected from at least one of, ceramide, suramin, rapamycin, paclitaxel, sirolimus, zotarolimus, everolimus, a therapeutic fluid, an anesthetic drug, a therapeutic drug, a small molecule, a gene therapeutic compound, an anti-thrombolytic agent, a lubricant (to allow higher temperatures without sticking), an electrically conductive compound to lower the impedance at an electrode, an electrically insulating compound to prevent treatment to tissue that does not need treatment, an electrically conductive compound that is intended to migrate through the endothelial layers of tissue to carry energy to the interstitial layers, or a combination of the above.

In yet another aspect, the invention comprises a method for selective fluid delivery in a lumen. The method includes engaging a body tissue disposed about the lumen with a plurality of fluid delivery channels on a radially expandable structure near a distal end of a catheter when the expandable structure expands, the balloon material is a membrane of a fixed pore size, and adding energy or heat to the fluid adjacent to the balloon surface allows the specific molecules to be passed through the membrane at the specific region for the specific time by virtue of the energy/heat source being switched on or off.

BRIEF DESCRIPTION OF THE DRAWINGS

FIGS. 4A and 4B schematically illustrates coatings covering the electrodes.

FIG. 5 schematically illustrates the used of aptamers in treating tissue.

FIG. 6 schematically illustrates placement of electrode pairs for use in bipolar energy treatment before, during, or after drug delivery.

DETAILED DESCRIPTION OF THE INVENTION

Figure 1:
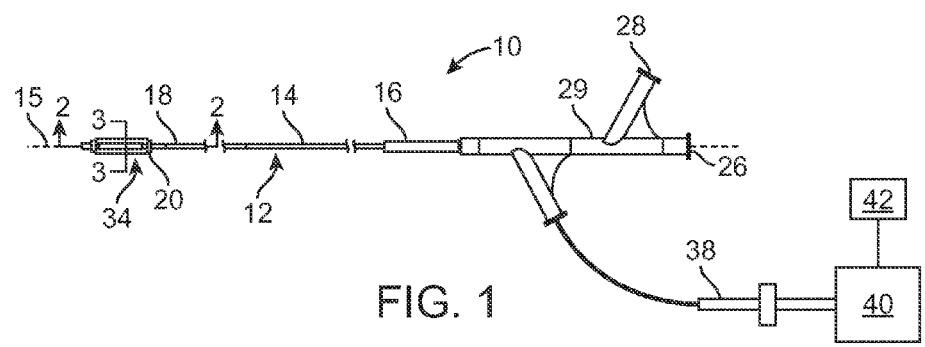
FIG. 1 schematically illustrates one embodiment of a catheter system having a coating for selective drug delivery to a body tissue being disposed about a lumen.

Many therapies have been developed to replace or improve upon traditional balloon angioplasty and stents. The alternative devices described in the BACKGROUND OF THE INVENTION either cut, ablate, or vaporize diseased tissue in an artery. For example, laser devices vaporize plaque and flush it downstream. Atherectomy devices excise plaque and suck it out of the body. Cutting balloons incise the artery wall, damaging the tissue. Even a simple angioplasty balloon does trauma to the tissue. It would be advantageous to provide treatments to body tissue that do not cut, ablate, or vaporize.

The present invention discloses systems and methods for selective delivery of a fluid to body tissue in a lumen, in particular, selective drug delivery in a lumen. Selective delivery may also control when and where the drug is delivered, and the amount of drug delivered.

While the disclosure focuses on drug delivery, such as, ceramide, suramin, rapamycin, paclitaxel, sirolimus, zotarolimus, everolimus, a drug (anesthetic or therapeutic), many other suitable fluids may be also be delivered to body tissue, for example, a therapeutic fluid, a small molecule, a gene therapeutic compound, an anti-thrombolytic agent, a lubricant (to allow higher temperatures without sticking), an electrically conductive compound to lower the impedance at the electrode, an electrically insulating compound to prevent treatment to tissue that does not need treatment, an electrically conductive compound that is intended to migrate through the endothelial layers of tissue to carry energy to the interstitial layers, or a combination of the above.

In some embodiments of the present invention, a drug is incorporated into a coating on a balloon catheter that is thermally released once inside the lumen to selectively treat the tissue. In other embodiments, a fluid or drug may be delivered through fluid delivery channels in a catheter system to selectively treat the tissue. In still other embodiments, multiple fluids or drugs may be delivered as part of a coating, through the fluid delivery channels, by thermal osmosis through a membrane, or any combination thereof. In some embodiments the drug may be delivered at one tissue site, while other embodiments portions of the drug to different sites.

Some embodiments of the present invention use heating to release the drug coating. Other embodiments combine fluid or drug delivery with heating of the tissue before, during or after delivery to the tissue. Devices for heating artery tissue using RF, ultrasound, microwave and laser energies have been disclosed in co-pending U.S. patent application Ser. Nos. 11/975,474, 11/975,383, 11/122,263 and U.S. Provisional Application No. 61/099,155, the full disclosures of which are incorporated herein by reference.

Drug Delivery During an Angioplasty Procedure

Some embodiments of the present invention provide systems and methods for drug delivery in a lumen in combination with heating during an angioplasty procedure. While drugs are disclosed, proteins, cells and/or molecules may also be delivered (discussed below). The angioplasty procedure itself is the procedure that will open the lumen. The heating will cause softening and shrinking of a lesion, enabling the plaque to reshape easily around the balloon while avoiding stretching of the vessel thus avoiding injury to the vessel. The drug will be released during the angioplasty procedure and the heating process. Drug delivery treatment during an angioplasty procedure will be a combination of:

Pressure—due to the balloon in order to open the lumen. The pressure may be standard angioplasty dilation pressures of 10-16 atmospheres or may be more gentle dilation pressures of 6 atmospheres or less, and possibly as low as 1 to 2 atmospheres.

Heating—due to the RF energy in order to soften and shrink the lesion. Heating may also have other benefits related to the drug or drug delivery (discussed below).

Drug/Protein/Cell/Molecule—which will be released during the procedure.

The Drug/Molecule/Protein/Cell element can be built of one component, or in combination of others such as:

1. Drugs: any molecule which will enable prevention or reduction of smooth muscle cell (SMC) proliferation and/or migration from the media to the intima, for example: ceramide, suramin, rapamycin and paclitaxel. The heating of the tissue may have a key role in helping deliver the drug into the lesion or tissue, and deeper into the media.

2. Proteins: proteins such as anti-inflammatory proteins, antibodies and other kinds of proteins which will enable the reduction and healing of the inflammation inside the lesion, or enable prevention or reduction of SMC proliferation and migration. We can also use protein that will induce cell apoptosis or oncosis. The heating may have a key role in activating these proteins during the treatment, and if heated quickly during the procedure, enabling the maximum time exposure of the tissue to the proteins. In order to make sure that the proteins will be activated during the procedure, one should take into account the half-life of a protein. The half-life of a protein is the time it takes before any half of the protein pool for that particular protein is left for human proteins, it ranges from minutes to 80 hours. In order to use proteins eluting balloon, the balloon needs to be maintained in lower temperature (<0° C.), so the proteins won't be ruined and destroyed. Several of the proteins that may be combined to a molecule named Adenosine-5'-triphosphate (ATP). ATP is a multifunctional nucleotide that is important as a "molecular currency" of intracellular energy transfer. In one example, the balloon is covered with the protein and the electrodes are covered with ATP (or the opposite) and the protein will be released with the balloon inflation, and the ATP will be released when the energy will be emitted from the electrodes (or the opposite).

3. Cells: coating the balloon with cells such as endothelium, or any other type of cell which can migrate to the lesion during the procedure, where they will release proteins or antibodies to heal the inflammation or prevent SMC proliferation and migration. The heat in this case is also to activate the cells during the procedure.

4. Molecules or proteins that can be attached or become activated when attached to heat shock proteins (HSP). HSP are a group of proteins whose expression is increased when the cells are exposed to elevated temperatures or other stress. For example, HSP27 functions in smooth muscle cells (SMC) migration. In this case the RF energy and the heating will result in elevation of HSP27 inside the SMC, so we can use any drug/molecule or protein directly to the SMC by using anti-HSP27 antibody. The concept is to use the heat and the outcomes of the heat in order to use other molecules or proteins to bind, degrade, inhibit or activate other proteins or cells in the lesion and in the media, in order to prevent restenosis.

Drug Delivery Coatings

FIG. 1 shows one embodiment of a catheter system 10 having a releasable coating for selective drug delivery to a body tissue being disposed about a lumen. The catheter system 10 includes a balloon catheter 12 having a catheter body 14 with a proximal end 16 and a distal end 18. Catheter body 14 is flexible and defines a catheter axis 15, and may include one or more lumens, such as a guidewire lumen 22 and an inflation lumen 24. Catheter 12 includes an inflatable balloon 20 adjacent distal end 18 and a housing 29 adjacent proximal end 16. Housing 29 includes a first connector 26 in communication with guidewire lumen 22 and a second connector 28 in fluid communication with inflation lumen 24. Inflation lumen 24 extends between balloon 20 and second connector 28. Both first and second connectors 26, 28 may optionally comprise a standard connector, such as a Luer-Loc™ connector. A distal tip may include an integral tip valve to allow passage of guidewires, and the like.

Housing 29 also accommodates an electrical connector 38. Connector 38 includes a plurality of electrical connections, each electrically coupled to electrodes 34 via conductors 36. This allows electrodes 34 to be easily energized, the electrodes often being energized by a controller 40 and power source 42, such as RF energy. In one embodiment, electrical connector 38 is coupled to an RF generator via a controller 40, with controller 40 allowing energy to be selectively directed to electrodes 34. While RF energy is disclosed, other suitable energy sources may be used, such as microwave energy, ultrasound energy, or laser energy, each having energy delivery portions configured to deliver the desired energy. See copending U.S. Provisional Application No. 61/099,155, the full disclosures of which are incorporated herein by reference.

In some embodiments, controller 40 may include a processor or be coupled to a processor to control or record treatment. The processor will typically comprise computer hardware and/or software, often including one or more programmable processor unit running machine readable program instructions or code for implementing some or all of one or more of the methods described herein. The code will often be embodied in a tangible media such as a memory (optionally a read only memory, a random access memory, a non-volatile memory, or the like) and/or a recording media (such as a floppy disk, a hard drive, a CD, a DVD, a non-volatile solid-state memory card, or the like). The code and/or associated data and signals may also be transmitted to or from the processor via a network connection (such as a wireless network, an Ethernet, an internet, an intranet, or the like), and some or all of the code may also be transmitted between components of catheter system 10 and within processor via one or more bus, and appropriate standard or proprietary communications cards, connectors, cables, and the like will often be included in the processor. Processor will often be configured to perform the calculations and signal transmission steps described herein at least in part by programming the processor with the software code, which may be written as a single program, a series of separate subroutines or related programs, or the like. The processor may comprise standard or proprietary digital and/or analog signal processing hardware, software, and/or firmware, and will typically have sufficient processing power to perform the calculations described herein during treatment of the patient, the processor optionally comprising a personal computer, a notebook computer, a tablet computer, a proprietary processing unit, or a combination thereof. Standard or proprietary input devices (such as a mouse, keyboard, touchscreen, joystick, etc.) and output devices (such as a printer, speakers, display, etc.) associated with modern computer systems may also be included, and processors having a plurality of processing units (or even separate computers) may be employed in a wide range of centralized or distributed data processing architectures.

Figure 2:
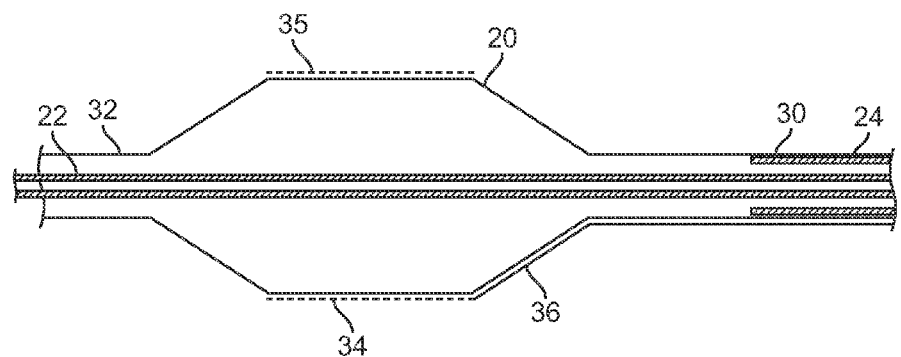
FIG. 2 schematically illustrates one embodiment of an inflatable balloon for use in the catheter system of FIG. 1.

Balloon 20 is illustrated in more detail in FIG. 2. Balloon 20 generally includes a proximal portion 30 coupled to inflation lumen 24 and a distal portion 32 coupled to guidewire lumen 22. Balloon 20 expands radially when inflated with a fluid or a gas. In some embodiments, the fluid or gas may be non-conductive and/or cooled. In some embodiments, balloon 20 may be a low pressure balloon pressurized to contact the artery tissue. In other embodiments, balloon 20 is an angioplasty balloon capable of higher pressure to both heat the artery tissue and expand the artery lumen. Balloon 20 may comprise a compliant or non-compliant balloon having helical folds to facilitate reconfiguring the balloon from a radially expanded, inflated configuration to a low profile configuration, particularly for removal after use.

Electrodes 34 are mounted on a surface of balloon 20, with associated conductors 36 extending proximally from the electrodes. Electrodes 34 may be arranged in many different patterns or arrays on balloon 20. The system may be used for monopolar or bipolar application of energy. For delivery of bipolar energy, adjacent electrodes are axially offset to allow bipolar energy to be directed between adjacent circumferential (axially offset) electrodes. In other embodiments, electrodes may be arranged in bands around the balloon to allow bipolar energy to be directed between adjacent distal and proximal electrodes.

Figure 3A:
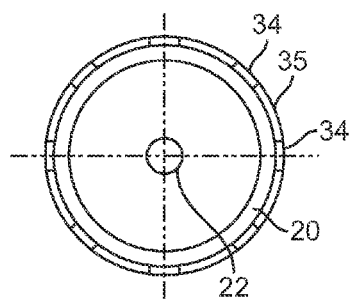
FIG. 3A schematically illustrates a cross-sectional view and 3B is an enlarged view of the balloon of FIG. 2.
Figure 3B:
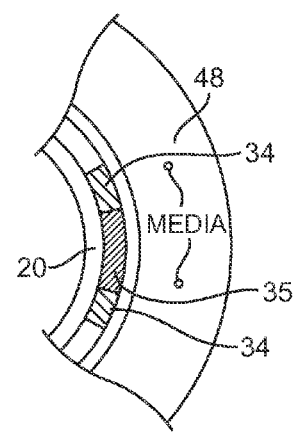

A coating 35 is coupled to the balloon 20 and positioned between electrodes 34, such as shown in FIGS. 3A and 3B. Coating 35 includes a fluid or drug to be delivered to the targeted tissue. It is envisioned that the coating will be thermally activated and configured to be released from the balloon surface at a temperature above body temperature (greater than 37 C). The idea is to have the energy delivery or heat, change the phase of a coating compound from a solid to a liquid, and releases the drug. This temperature increase involves activating electrodes 34 using RF energy. As the energy is increased, the coating 35 between the electrodes 34 is heated and released thermally to the local tissue 48. Coating 35 is durable or flexible such that it can be folded with the balloon 20 without separation or delamination. This mechanism could release small or large molecular drug or pharma product. The drug could be in a solid gel form.

In some embodiments, a second coating 35A may be used to cover electrodes 34, such as shown in FIG. 4A. Second coating 35A may be an insulating coating on the electrodes 34. The second coating 35A would be used when treating inside a metallic object in the lumen, such as a stent, because if the electrodes 34 come in contact with metal, they may short and the treatment will end. If the electrodes 34 are coated with a material with electrical properties such that the electrodes can not be shorted with metallic objects, the treatment can continue even when in contact with metal objects. This would allow catheter system 10 to treat inside objects like stents. Second coating 35A may also act to insulate electrodes 34 from tissue 48, shown in FIG. 4B, which stops/prohibits energy flow through tissue 48 and sends the energy through coating 35, heating only the coating 35 between the electrodes 34, releasing the drug to the tissue 48. The second coating 35A may also include a different drug than coating 35.

Many types of drugs may be included in the coatings. For example, the coating may include drugs currently used in drug eluding stents, such as sirolimus (used in the Cypher™ stent), paclitaxel (used in the Taxus™ stent), zotarolimus (used in the Endeavour™ stent) and everolimus (used in the Xience V™ stent).

Some embodiments of the present invention may include aptamers 52 coated to the balloon 20 using a substrate that breaks down readily when heated, such as when the RF energy source is activated. Aptamers can be engineered to bind very specifically to various molecular targets such as small molecules, proteins, nucleic acids, and even cells, tissues and organisms. The aptamers 52 could be synthesized to bind 54 with desired tissue 48 to be treated, such as plaque, within the lumen or artery.

While the catheter system 10 is not powered and the balloon 20 deflated, the coating 35 with aptamers 52 would remain on the balloon 20. Once the balloon 20 is inflated and the energy unit turned on, the coating is released and the aptamers 52 bind to the desired tissue, such as shown in FIG. 5. In some embodiments, aptamers 52 would be conjugated to a microscopic bead 56 that is highly receptive to the energy 58, such as RF energy, emitted by the catheter system 10. The beads 56 convert the RF energy to thermal energy directly and only to the tissue that the aptamers 52 is in contact with.

Aptamers are nucleic acids that bind to the surface of molecules in much the same way as antibodies. One importance difference between aptamers and antibodies is that aptamers can be produced by chemical synthesis whereas antibodies are produced biologically, first animals, then in culture or an expression system. Another important difference is that aptamers are very stable and not sensitive to their surrounding environment, including temperature.

In some embodiments, coating 35 may include a chemical solvent that has plaque softening properties. Ether, chloroform, benzene, and acetone are known to be lipid solvents. Furthermore, amino acids, proteins, carbohydrates, and nucleic acids are largely insoluble in these solvents. If the solvent is used in conjunction with tissue heating, the tissue treatment may require less energy over a shorter time period, lessening the chance of damage to healthy tissue. If the tissue includes calcium deposits, the same process used to deliver lipid solvents to plaque could be used to deliver calcium solvents to calcification sites. Calcium is highly soluble in a variety of organic solvents. In both cases, the solvent would be coupled to the surface of the balloon with a coating that would break down either with the application of heat or RF energy, or as the balloon is inflated.

In some embodiments, the coating may incorporate more than one drug, agent, or fluid listed herein within the coating, each having different phase change temperatures. For example, an anesthetic could be administered at a lower melting temperature prior to a specific treatment of higher temperature where there may be a nerve in the general location. Is some embodiments, two coatings of differing material may be used, such as by layering. For example, a first layer may include a first drug that attaches to the target tissue and act as a receptor to a second drug in a second layer. In some embodiments the coating is non-conductive to reduce or eliminate electrical shorts between electrodes.

In some embodiments, tissue signature could be used to identify treatment regions with the use of impedance measurements. Impedance measurements utilizing the radially spaced electrodes 34 within a lumen can be used to analyze tissue. Impedance measurements between pairs of adjacent electrodes (and/or between pairs of separated electrodes), may differ when the current path passes through diseased tissue, and when it passes through healthy tissues of the luminal wall. Hence, impedance measurements between the electrodes on either side of diseased tissue may indicate a lesion, while measurements between other pairs of adjacent electrodes indicate healthy tissue. Other characterization, such as intravascular ultrasound, optical coherence tomography, or the like may be used to identify regions to be treated.

Some embodiments described herein may be used to treat atherosclerotic disease by selective drug delivery in combination with "gentle heating" utilizing the "Q10 Rule" to further enhance the fluid or drug treatment. Under the Q10 Rule, it is well known that rates of biochemical reactions usually double when temperature is increased by 10° C.

As shown in FIG. 6, electrodes 34 are positioned circumferentially around the balloon 20. RF energy 43 is directed to electrodes adjacent pairs of electrodes 34A and 34C, or 34A and 34D, or any combination of 34A-34D, treating both the healthy tissue 45 and atherosclerotic material 48 within lumen 50. This arrangement creates an energy path 43 through the tissue that delivers energy or heat ("tissue remodeling energy") in particular treatment zones or segments to the artery tissue between the electrode pairs ("remodeling zones") having a volume between the electrode pairs at a specific depth. Using different combinations of electrode pairs may reduce or eliminate gaps between the remodeling zones by using overlapping pairs. Using electrode pairs with bipolar energy may avoid some potential issues of the monopolar approach. Diseased artery tissue 48 has a higher electrical resistivity than healthy artery tissue. By using pairs of electrodes 34A, 34B in a bipolar system, tissue remodeling energy will go through the healthy tissue, diseased tissue, or a combination of both healthy and diseased tissues between the electrode pairs in the remodeling zones. Any number of electrode pairs may be used in different patterns or arrays to create a number of remodeling zones. The controller may apply either constant power, constant current, or constant voltage, whichever has the most advantage.

The controller 40 may energize the electrodes with about 0.25 to 5 Watts average power for 1 to 180 seconds, or with about 4 to 45 Joules. Higher energy treatments are done at lower powers and longer durations, such as 0.5 Watts for 90 seconds or 0.25 Watts for 180 seconds. Most treatments in the 2 to 4 Watt range are performed in 1 to 4 seconds. Using a wider electrode spacing, it would be appropriate to scale up the power and duration of the treatment, in which case the average power could be higher than 5 Watts, and the total energy could exceed 45 Joules. Likewise, using a shorter or smaller electrode pair would require scaling the average power down, and the total energy could be less than 4 Joules. The power and duration are calibrated to be less than enough to cause severe damage, and particularly less than enough to ablate diseased tissue 48 within a blood vessel.

In some embodiments the delivery of the drug and gentle heat may be accompanied by balloon angioplasty using gentle dilation to remodel the artery with dilation pressures which are at or significantly lower than standard, unheated angioplasty dilation pressures. Where balloon inflation pressures of 10-16 atmospheres may, for example, be appropriate for standard angioplasty dilation of a particular lesion, modified dilation treatments combined with appropriate electrical potentials (through flexible circuit electrodes on the balloon, electrodes deposited directly on the balloon structure, or the like) described herein may employ from 10-16 atmospheres or may be effected with pressures of 6 atmospheres or less, and possibly as low as 1 to 2 atmospheres. Such moderate dilations pressures may (or may not) be combined with one or more aspects of the tissue characterization, tuned energy, eccentric treatments, and other treatment aspects described herein for treatment of diseases of the peripheral vasculature.

Covalently Bound BioMolecules

Current endovascular therapies for preventing or permanently removing hyperplastic neointima are not completely efficacious. While removal of such tissue is achieved by multiple such therapies, regrowth of the tissue is a frequent occurrence, leading to restenosis and dysfunctional blood flow. Drug-eluting stents are able to inhibit the frequency of restenosis, but fall short of completely restoring vascular function, owing to the presence of a persistent implant; the stent.

More recently, drug clotting balloons have shown an even greater reduction in the frequency of restenosis than drug eluting stents and are removed after treatment, however, high pressure inflation is required to optimally deliver the anti-proliferation/anti-inflammatory biomolecules. The molecules may function to prevent restenosis by preventing inflammatory cell influx (chemo taxis), cell proliferation. The molecules may also function to stabilize the IEL matrix by providing structural support, thus "setting" the lumen diameter.

Figure 9A:
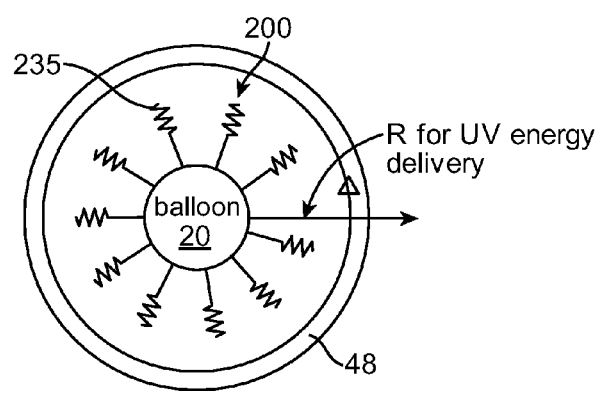
FIGS. 9A and 9B schematically illustrate cross-sectional views showing tissue treatment using biomolecules having a thermally releasable active portion and an inert portion coupled by covalent bond to a balloon surface.
Figure 9B:
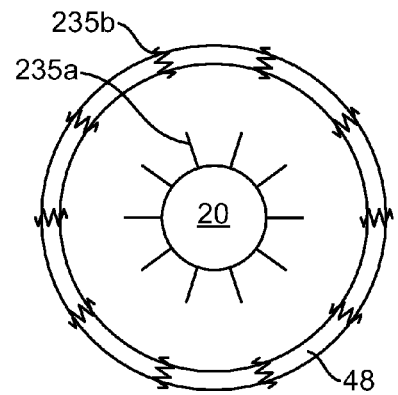

FIGS. 9A and 9B show another embodiment of a catheter system 200 for drug delivery to a body tissue 248. The system 200 is similar to system 10 above, except the use of biomolecules 235 coupled to the balloon 20 instead of a coating. The biomolecules 235 include a thermally releasable active portion 235a and an inert portion 235b coupled by covalent bond to a balloon 20 surface. The active portion or molecule 235b is capable of treating the desired tissue 248, which may be enhanced with temperature or pressure. The inert portion 235a of the biomolecule stays on the balloon. The embodiment described herein utilizes a radiofrequency endovascular balloon catheter that, upon low pressure inflation and energy delivery from the balloon to the atherosclerotic lesion, hyperthermally releases the active portion of the biomolecule that is covalently bound to the balloon, thus, delivering the active portion of the molecule to the targeted tissue. The energy may also include ultrasound emitting energy. The active molecule 235b functions to prevent production of hyperplastic tissue by any means, including, but not limited to, cytostasis (prevention of mitosis), receptor maturation (i.e., those receptors at/on cells on the targeted tissue that are adhesive to/for a chemotactic to/for infiltrating cells that promote hyperplasic tissue formation.

The molecule's bioactive portion 235b is released from the intact biomolecule 235 by delivery of energy (such as from electrodes 34) that induces a local hyperthermia environment. The molecule is stable under the hyperthermia conditions. The molecule can prevent one or all of the following functions:

cell proliferation:
cell function:
receptor-ligand binding:
chemotaxis of inflammatory cells to the target tissue and migration of cells in the native artery strata to the diseased tissue.

The influx of the molecule 235b into the diseased tissue 48 is facilitated and/or hastened by the energy mediated hypothermia, i.e., cleavage from the intact biomolecule, migration into the diseased tissue, and residence in the diseased tissue by virtue of increased porosity are all accelerated by the hyperthermia.

This invention uniquely delivers a bioactive molecule into diseased tissue with:

greater speed, by hypothermal acceleration:
more completeness, by rendering the diseased tissue more receptive/porous to the molecule: and/or
with no inactive segments of the biomolecule, i.e., no polymer, inactive protein sequence/segment, or co-factors required for activation left at the treatment site (the inactive segments stay on the balloon).

Clinical application and uses are designed to reduce plaque, inhibit restenosis in stented or not-stented site, and may be used as an adjunctive treatment to aggressive non-implantable endovascular procedures and stent implants.

Fluid Delivery Channels

Figure 7:
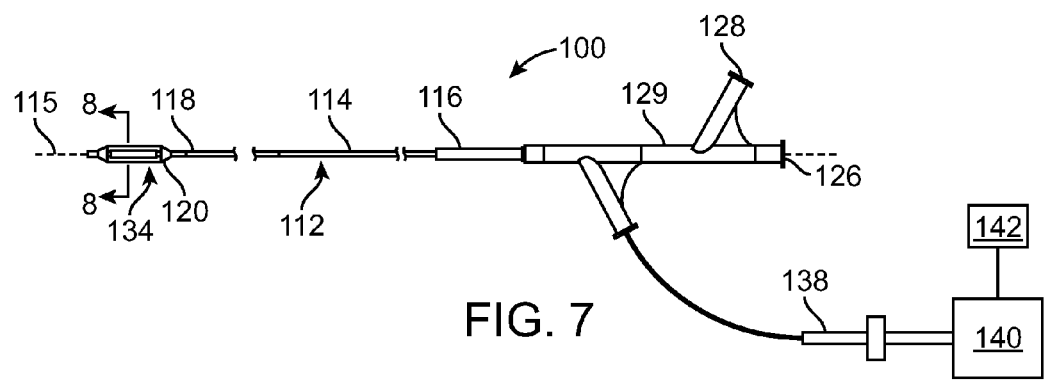
FIG. 7 schematically illustrates another embodiment of a catheter system having fluid delivery channels for selective fluid delivery to a body tissue being disposed about a lumen.

FIG. 7 shows another embodiment of a catheter system 100 having fluid delivery channels for selective fluid delivery to a body tissue being disposed about a lumen. The catheter system 100 includes a balloon catheter 112 having a catheter body 114 with a proximal end 116 and a distal end 118. Catheter body 114 is flexible and defines a catheter axis 115, and may include one or more lumens, such as a guidewire lumen 122 and an inflation lumen 124. Catheter 112 includes an inflatable balloon 120 adjacent distal end 118 and a housing 129 adjacent proximal end 116. Housing 129 includes a first connector 126 in communication with guidewire lumen 122 and a second connector 128 in fluid communication with inflation lumen 124. Inflation lumen 124 extends between balloon 120 and second connector 128. Both first and second connectors 126, 128 may optionally comprise a standard connector, such as a Luer-Loc™ connector. A distal tip may include an integral tip valve to allow passage of guidewires, and the like.

Housing 129 also accommodates an electrical connector 138. Connector 138 includes a plurality of electrical connections, each electrically coupled to electrodes 134 via conductors 136. This allows electrodes 134 to be easily energized, the electrodes often being energized by a controller 140 and power source 142, such as RF energy, microwave energy, ultrasound energy, or other suitable energy sources. In one embodiment, electrical connector 138 is coupled to an RF generator via a controller 140, with controller 140 allowing energy to be selectively directed to electrodes 134 or electrode pairs. Controller 140 may include a processor or be coupled to a processor to control or record treatment.

Figure 8A:
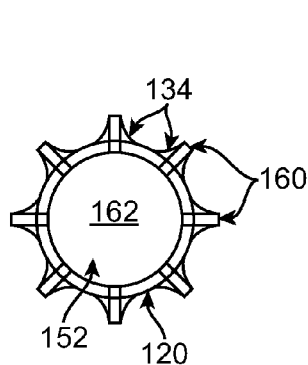
FIG. 8A schematically illustrates a cross-section and FIG. 8B is an enlarged section of the balloon in FIG. 7 showing fluid delivery channels through the balloon coupled to electrodes mounted on a surface of the balloon.
Figure 8B:
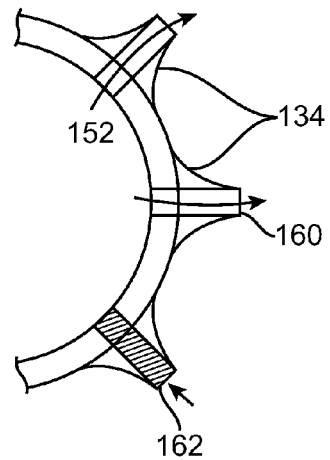

FIG. 8A shows a cross-section of the balloon 120 and FIG. 8B is an enlarged section showing fluid delivery channels 160 through the balloon 120 coupled to electrodes 134 mounted on a surface of balloon 120. Electrodes 134 include associated conductors extending proximally from the electrodes. Electrodes 134 and fluid delivery channels 160 may be arranged in many different patterns or arrays on balloon 120. Fluid delivery channels 160 may be coupled to a fluid reservoir or lumen 162 holding the fluid 152. In some embodiments, the inflation medium may contain the fluid to be delivered. In some embodiments, the channels 160 thru balloon 120 may be filled with wax-like material 164 that can be expelled thermally in order to open the channel (or any other material that can be expelled). In other embodiments, electrodes 134 may open and close a flap to release the fluid.

The delivery channels 160 may protrude from the balloon surface such that they are capable of penetrating the body tissue of the lumen. In some embodiments, the electrodes may penetrate the body tissue.

The catheter system 100 may also include a tissue analyzer configured to characterize the body tissue. In some embodiments, electrodes 134 may be sensing electrodes, as discussed above, that could help characterize the tissue to identify regions the be treated or not using electrical impedance tomography. Other characterization, such as intravascular ultrasound, optical coherence tomography, or the like may be used to identify regions to be treated. Electrodes 134 may be energized in response to the characterized body tissue Some embodiments described herein may be used to treat atherosclerotic disease by selective fluid delivery in combination with "gentle heating" to further enhance the fluid delivery or treatment, as discussed above.

Electrodes 134 may be selectively energized to open or close fluid delivery channels 160 to treat tissue. One method includes opening the fluid delivery channels 160 by selectively heating the electrodes (by Joule heating or other means, including inducing a heightened temperature in the adjacent region, whereby hear transfer could heat the electrode(s)), such that a material 164, that would otherwise block the channel, is phase changed from solid to liquid. Another possible method may include the use of MEMS (micro-electormechanical-systems) to open and/or close channels 160 selectively.

In some embodiments, the fluid delivery channels may be vias through the electrodes (perfused electrodes). The vias or small holes may be used to deliver a fluid to the artery tissue proximate the electrode. The holes may be less than 1 µm in diameter and may be made with a laser or ion beam. The holes may be made in the electrodes and balloon. In one example, electrode pads on a flexible circuit are designed with vias that are plated. The flexible circuit is mounted on a balloon and a laser or ion beam is used to create the holes in the flexible substrate and balloon. There may be several holes in the flexible/balloon for every electrode pad. The balloon may then be perfused with standard perfusion balloon equipment or specialized equipment. This perfusion approach may also provide additional advantages beyond fluid delivery, such as eliminating sticking, carry away heat or regulate the impedance of the load.

In some embodiments, a porous balloon may be used having fluid delivery channels on a micro-level, allowing select molecules through with the addition of heat. The porous balloon may have an inner layer, a porous outer layer or membrane, drug or fluid molecules positioned between the layers (i.e., a reservoir) and electrodes coupled to the outer layer. At low pressures, the molecules stay within the reservoir. As heat is applied, the molecules may go through the porous layer, which may be done in different ways. For example, as the heat is applied, the drug molecules may become exited, providing enough force to go through the porous outer layer. In another example, as heat is applied to the balloon, the pores expand, allowing the drug molecules to go through the porous outer layer. The molecules may also pass through the porous outer layer or membrane by osmotic pressure along with the heat.

In some embodiments, the treatments may include a drug, and/or thermal, and/or small or large molecules injection, and/or RF, and/or balloon dilatation, and/or hyperthermia.

While the devices, systems, and methods disclosed herein discuss a balloon as the radially expandable structure, other expandable structures may also be used, such as described in U.S. patent application Ser. Nos. 11/975,651, the full disclosure of which is incorporated herein by reference.

Thermally Excited Ozmolarity

In some embodiments, a porous balloon may be used having fluid delivery channels on a micro-level in a membrane, allowing molecules through with the addition of pressure and heat. The concept delivers a fluid or drug to a specific site by passing it through the membrane, much like reverse osmosis. In reverse osmosis, a pressure is used to drive a liquid, such as water, through a membrane with passages so small that only the appropriate molecules can pass through. In this embodiment, the membrane barrier retains a drug, like paclitaxel. At low pressures, the drug molecules are not able to pass through the membrane. To release the drug through the membrane, pressure is applied to the drug molecules using a balloon the release of the drug is the accelerated by applying energy locally by an electrode pair or monopolar electrode.

Figure 10:
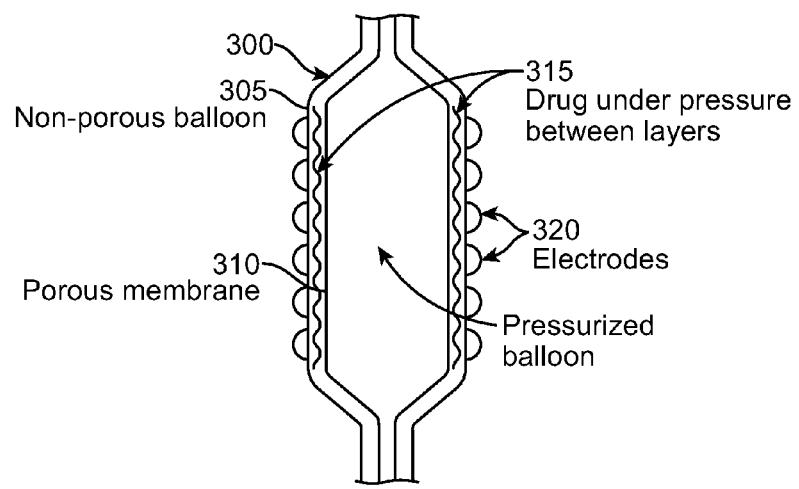
FIG. 10 schematically illustrates another embodiment of a balloon having a membrane for selective drug delivery to a body tissue being disposed about a lumen.

FIG. 10 shows one embodiment of a catheter system, similar to catheter system 10, having a balloon 300 with a non-porous inner balloon 305 (to provide pressure), a porous outer layer, membrane or sleeve 310, a drug or fluid 315 positioned between inner balloon 305 and membrane 310 (i.e., a reservoir), and electrodes 320 coupled to the membrane 310. Electrodes 320 may be similar to the electrodes describe above.

In use, the balloon is placed at the desired tissue site and the balloon is inflated to a suitable pressure, such as 4-6 ATM. When the electrodes are energized, the heat energy causes the membrane pores to open and the drug molecule to excite and make their way through the pores to the tissue.

The devices, systems, and methods disclosed herein may be used to selectively deliver fluid in any artery, for example, the femoral, popliteal, coronary and/or carotid arteries. While the disclosure focuses on the use of the technology in the vasculature, the technology would also be useful for any luminal obstruction. Other anatomical structures in which the present invention may be used are the esophagus, the oral cavity, the nasopharyngeal cavity, the auditory tube and tympanic cavity, the sinus of the brain, the arterial system, the venous system, the heart, the larynx, the trachea, the bronchus, the stomach, the duodenum, the ileum, the colon, the rectum, the bladder, the ureter, the ejaculatory duct, the vas deferens, the urethra, the uterine cavity, the vaginal canal, and the cervical canal.

The devices, systems, and method disclosed herein may employ one or more of a wide variety of mechanisms to facilitate, promote, and/or enhance transport of at least one drug from a fluid, gel, or solid of a catheter (or other delivery structure) toward, to and/or into a desired treatment site or tissue. Exemplary thermally-mediated drug transport mechanisms which may be employed are described above. Additional mechanisms may also be used including electrically mediated drug transport mechanisms, optionally including mechanisms such as electroporation, ionotophoresis, and the like. Electroporation may allow targeting drug molecules intracellularly via creating passages in the cell membrane. Electroporation can significantly increase the electrical conductivity and permeability of the cell plasma membrane by application of an external electrical field, optionally by application of an electroporation voltage (which may involve a series of electroporation potentials) using one or more electrodes of the balloon catheters described herein. Iontophoresis may be employed by applying a relatively small electric potential so as to deliver a medicine or other chemical through the luminal surface, with the electrical potential again optionally being applied using one or more electrodes of the balloon catheters described hereinabove. As another example, anti-inflammatory molecules could be delivered via iontophoretic membranes to atherosclerotic lesions. Small molecule inhibitors of inflammation, thrombogenesis, and thrombosis can be delivered to atheroloscrotic lesions via iontophoretic methods using devices and systems described herein to slow or prevent progression of atherosclerosis and thrombus formation. Examples of suitable inflammatory and/or thrombogenic tissue targets in the artery may include platelet cell adhesion factor (PECAM), Tissue Factor (TF), matrix metalloproteinases (MMP), and/or the like. Examples of a small molecule anti-inflammatory/anti-thrombosis therapeutics that would be amenable to delivery via iontophoresis may include heparin, heparin sulfate, and/or the like. Advantageously, suitable potentials may be applied in either a bipolar arrangement (between electrodes of the balloon catheter) or in a monopolar mode. Suitable potentials may be applied by commercially available iontophoresis or electroporation systems, or specialized potential generators may be employed. These drug transport mechanisms can optionally be combined, for example, with a thermal mechanism used (for example, by energizing electrodes so as to heat a coating, and optionally to facilitate release of a drug and thermally enhance movement of the drug into a target tissue), followed with an electrically mediated drug transport mechanism (optionally by energizing the same electrodes or different electrodes of the balloon with a suitable potential).

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. A catheter system for selective drug delivery to a body tissue being disposed about a lumen, the system comprising:
    an elongate catheter having a proximal end and a distal end with an axis therebetween, the catheter having a radially expandable balloon near the distal end and an energy delivery portion proximate the balloon for transmission of energy, wherein the energy delivery portion comprises a plurality of electrodes mounted on a surface of the expandable balloon;
    a thermally changeable coating having a releasable drug coupled to the balloon, the thermally changeable coating being oriented to be urged against the body tissue when the expandable balloon expands; and
    an energy source operatively coupled to the plurality of electrodes with a controller configured to selectively energize one or more electrodes of the plurality of electrodes to selectively heat and liquefy a portion of the thermally changeable coating to release the drug to the body tissue, wherein the portion is less than the entire coating,
    wherein the plurality of electrodes comprise a plurality of bipolar electrode pairs disposed about the expandable balloon, the controller configured to selectively energize selected electrode pairs of the plurality to heat and liquefy portions of the thermally changeable coating between the electrode pairs to release the drug to the body tissue.

2. The system of claim 1, wherein the body tissue of the lumen includes a diseased portion and select electrode pairs are energized to selectively heat the thermally changeable coating proximate the diseased portion.

3. The system of claim 1, wherein the energy delivery portion comprises a plurality of electrodes disposed about the expandable balloon so as to define a plurality of remodeling zones in the tissue when the balloon is expanded within the lumen, the electrodes being radially coupled with the tissue so that energy is transmitted between the electrodes and the tissue.

4. The system of claim 1, further comprising a tissue analyzer configured to characterize the body tissue using the plurality of electrodes.

5. The system of claim 4, wherein the controller is configured to selectively energize the one or more electrodes to heat the thermally changeable coating to release the drug in response to a characterization of the body tissue by the tissue analyzer.

6. The system of claim 1, wherein the energy delivery portion is energized to heat the body tissue before, during and/or after the drug delivery.

7. The system of claim 1, wherein the thermally changeable coating includes more than one releasable drug.

8. The system of claim 1, wherein the drug includes any of a lubricant to allow higher temperatures without sticking, an electrically conductive compound to lower the impedance at an electrode, an electrically insulating compound to prevent treatment to tissue that does not need treatment, an electrically conductive compound that is intended to migrate through the endothelial layers of tissue to carry energy to the interstitial layers, or a combination of the above.

9. The system of claim 1, wherein the energy source is a RF energy source and the energy delivery portion is configured to transmit RF energy.

10. A method for selective drug delivery in a lumen, the method comprising:
    engaging a body tissue disposed about the lumen with a thermally changeable coating having a releasable drug disposed on a radially expandable balloon near a distal end of a catheter when the expandable balloon expands, wherein the balloon includes an energy delivery portion comprising a plurality of electrodes mounted on a surface of the balloon;

selectively energizing one or more electrodes of the plurality of electrodes so as to heat and liquefy a select portion of the thermally changeable drug coating, wherein the portion is less than the entire coating; and releasing the drug from the heated portion of the thermally changeable coating into the body tissue, wherein the plurality of electrodes comprises a plurality of bipolar electrode pairs disposed about the expandable balloon and selectively energizing one or more electrodes comprises selectively energizing selected electrode pairs of the plurality so as to heat and liquefy portions of the thermally changeable drug coating between the selected electrode pairs.

11. The method of claim 10, wherein the body tissue of the lumen includes a diseased portion and select electrode pairs are energized to heat the thermally changeable coating proximate the diseased portion.

12. The method of claim 10, further comprising characterizing the body tissue using the plurality of electrodes to identify body tissue to be treated and selectively heating portions of the thermally changeable coating to release the drug in response to the characterized body tissue to treat the identified body tissue.

13. The method of claim 10, further comprising heating the body tissue before, during and/or after the drug delivery.

14. The method of claim 10, wherein the drug includes any of a lubricant to allow higher temperatures without sticking, an electrically conductive compound to lower the impedance at an electrode, an electrically insulating compound to prevent treatment to tissue that does not need treatment, an electrically conductive compound that is intended to migrate through the endothelial layers of tissue to carry energy to the interstitial layers, or a combination of the above.

15. The method of claim 10, wherein the energy delivery portion is energized with RF energy.

16. A catheter system for drug delivery to a body tissue being disposed about a lumen, the system comprising:

an elongate catheter having a proximal end and a distal end with an axis therebetween, the catheter having a radially expandable balloon near the distal end and an energy delivery portion proximate the balloon for transmission of energy, wherein the energy delivery portion comprises a plurality of electrodes mounted on a surface of the balloon;

a plurality of biomolecules having a thermally releasable drug component and an inert component covalently bound to the balloon; and an energy source operatively coupled to the plurality of electrodes with a controller configured to selectively heat a select portion of the balloon and the associated biomolecules coupled thereto so as to release the drug portion to the body tissue, wherein the portion is less than the entire balloon, wherein the plurality of electrodes comprises a plurality of bipolar electrodes disposed about the expandable balloon, the controller configured to selectively energize selected electrode pairs to heat portions of the balloon between the selected electrode pairs so as to heat the associated biomolecules to release the drug portion to the body tissue.

17. The system of claim 16, wherein the body tissue of the lumen includes a diseased portion and select electrode pairs are energized to selectively heat the biomolecules proximate the diseased portion.

18. The system of claim 16, wherein the biomolecules are oriented to be urged against the body tissue when the expandable balloon expands.

19. The system of claim 16, further comprising a tissue analyzer configured to characterize the body tissue using the plurality of electrodes.

20. The system of claim 19, wherein the controller is configured to selectively energize the one or more electrodes to heat the biomolecules to release the drug component in response to a characterization of the body tissue by the tissue analyzer.

21. The system of claim 16, wherein the energy delivery portion is energized to heat the body tissue before, during and/or after the drug delivery.

22. The system of claim 16, wherein the biomolecules include more than one releasable drug.

23. The system of claim 16, wherein the drug portion includes any of a lubricant to allow higher temperatures without sticking, an electrically conductive compound to lower the impedance at an electrode, an electrically insulating compound to prevent treatment to tissue that does not need treatment, an electrically conductive compound that is intended to migrate through the endothelial layers of tissue to carry energy to the interstitial layers, or a combination of the above.

24. A method for drug delivery in a lumen, the method comprising:

engaging a body tissue disposed about the lumen with a plurality of biomolecules having a thermally releasable drug component and an inert component covalently bound to the balloon near a distal end of a catheter when the expandable balloon expands, wherein the balloon includes an energy delivery portion comprising a plurality of electrodes mounted to a surface of the balloon;

selectively energizing one or more electrodes of the plurality so as to heat a select portion of the balloon and the associated biomolecules bound thereto, the select portion being less than the entire balloon; and releasing the drug component from the biomolecules into the body tissue, wherein the plurality of electrodes comprises a plurality of bipolar electrode pairs disposed about the expandable balloon and wherein selectively energizing the one or more electrodes comprises selectively energizing select electrode pairs of the plurality so as to heat the biomolecules in the portion of the balloon between the select electrode pairs to release the drug component in the portion to the body tissue.

25. The method of claim 24, further comprising heating the body tissue before, during and/or after the drug delivery.

26. The method of claim 24, further comprising characterizing the body tissue with the plurality of electrodes to identify body tissue to be treated and selectively energizing the one or more electrodes to heat the biomolecules to release the drug portion in response to the characterized body tissue to treat the identified body tissue.

27. A catheter system for selective fluid delivery to a body tissue being disposed about a lumen, the system comprising:

an elongated flexible catheter body having a proximal end and a distal end;

a radially expandable structure near the distal end of the catheter body having a plurality of electrodes mounted thereon;

a plurality of fluid delivery channels oriented to be urged against the body tissue when the expandable structure expands, the fluid delivery channels being initially blocked with a thermally changeable material; and an energy source connector operatively coupled to the plurality of electrodes proximate the fluid delivery channels with a controller configured to selectively energize one or more electrodes of the plurality so as to heat and liquefy the thermally changeable material to selectively open a portion of the fluid delivery channels for fluid release, the portion being less than all the fluid delivery channels.

28. The system of claim 27, wherein the plurality of fluid delivery channels protrude from the expandable structure to penetrate the body tissue of the lumen.

29. The system of claim 27, further comprising a tissue analyzer configured to characterize the body tissue using the plurality of electrodes.

30. The system of claim 29, wherein the fluid delivery channels can be selectively energized to selectively open one or more fluid delivery channels in response to the characterized body tissue.

31. The system of claim 27, wherein the radially expandable structure comprises a balloon and the fluid delivery channels are mounted on a circumference of the balloon.

32. The system of claim 27, wherein the radially expandable structure comprises an expandable basket and the fluid delivery channels are mounted on a circumference of the basket.

33. The system of claim 27, wherein the body tissue of the lumen includes a diseased portion and wherein the controller is configured to selectively energize select electrodes to selectively open one or more fluid delivery channels proximate the diseased portion.

34. The system of claim 27, wherein the controller is configured to selectively energize select electrodes to heat the body tissue in conjunction with the release of the fluid in the lumen.

35. The system of claim 27, wherein the fluid includes any of a lubricant to allow higher temperatures without sticking, an electrically conductive compound to lower the impedance at an electrode, an electrically insulating compound to prevent treatment to tissue that does not need treatment, an electrically conductive compound that is intended to migrate through the endothelial layers of tissue to carry energy to the interstitial layers, or a combination of the above.

36. A catheter system for selective fluid delivery to body tissue being disposed about a lumen, the system comprising:
an elongated flexible catheter body having a proximal end and a distal end;
a radially expandable structure near the distal end of the catheter body;
a plurality of fluid delivery channels oriented to be urged against the body tissue of the lumen when the expandable structure expands, the fluid delivery channels being initially closed; and
a plurality of micro-electromechanical systems (MEMS) coupled to the fluid delivery channels with a controller configured to selectively activate one or more MEMS of the plurality so as to open one or more fluid delivery channels and release a fluid in the lumen.

37. The system of claim 36, wherein the fluid includes any of a lubricant to allow higher temperatures without sticking, an electrically conductive compound to lower the impedance at an electrode, an electrically insulating compound to prevent treatment to tissue that does not need treatment, an electrically conductive compound that is intended to migrate through the endothelial layers of tissue to carry energy to the interstitial layers, or a combination of the above.

38. A method for selective fluid delivery in a lumen, the method comprising:
engaging a body tissue disposed about the lumen with a plurality of fluid delivery channels on a radially expandable structure near a distal end of a catheter when the expandable structure expands;
selectively opening one or more fluid delivery channels such that at least some of the fluid delivery channels remain closed; and
releasing a fluid from the select fluid delivery channels into the lumen,
wherein selectively opening one or more fluid delivery channels comprises selectively energizing electrodes coupled to the select fluid delivery channels to heat the select fluid delivery channels to liquefy a thermal material initially closing the fluid delivery channel.

39. The method of claim 38, wherein the one or more fluid delivery channels comprises a plurality of micro-electromechanical systems (MEMS) coupled to the fluid delivery channels configured to selectively open and/or close the fluid delivery channels.

40. The method of claim 38, further comprising characterizing the body tissue to identify body tissue to be treated and selectively opening or closing one or more fluid delivery channels in response to the characterized body tissue to treat the identified body tissue.

41. The method of claim 38, wherein the plurality of fluid delivery channels are configured to penetrate into the lumen wall.

42. The method of claim 38, wherein the radially expandable structure comprises a balloon and the fluid delivery channels are mounted on a circumference of the balloon.

43. The method of claim 38, wherein the radially expandable structure comprises an expandable basket and the fluid delivery channels are mounted on a circumference of the basket.

44. The method of claim 38, further comprising heating the body tissue in conjunction with releasing the fluid.

45. The method of claim 38, wherein the fluid includes any of a lubricant to allow higher temperatures without sticking, an electrically conductive compound to lower the impedance at an electrode, an electrically insulating compound to prevent treatment to tissue that does not need treatment, an electrically conductive compound that is intended to migrate through the endothelial layers of tissue to carry energy to the interstitial layers, or a combination of the above.

* * * * *